(12) United States Patent
Mehi et al.

(10) Patent No.: US 7,255,678 B2
(45) Date of Patent: Aug. 14, 2007

(54) HIGH FREQUENCY, HIGH FRAME-RATE ULTRASOUND IMAGING SYSTEM

(75) Inventors: James I. Mehi, Thornhill (CA); Nicholas Christopher Chaggares, Peterborough (CA); Stuart Foster, Toronto (CA); Robert McConaghy, Kirkland, WA (US)

(73) Assignee: VisualSonics Inc., Toronto (CA)

( * ) Notice: Subject to any disclaimer, the term of this patent is extended or adjusted under 35 U.S.C. 154(b) by 31 days.

(21) Appl. No.: 10/683,890

(22) Filed: Oct. 10, 2003

(65) Prior Publication Data

US 2004/0122319 A1 Jun. 24, 2004

Related U.S. Application Data

(60) Provisional application No. 60/470,234, filed on May 14, 2003, provisional application No. 60/468,956, filed on May 9, 2003, provisional application No. 60/468,958, filed on May 9, 2003, provisional application No. 60/417,164, filed on Oct. 10, 2002.

(51) Int. Cl.
*A61B 8/00* (2006.01)

(52) U.S. Cl. .................................................... 600/446

(58) Field of Classification Search ........ 600/443–446, 600/459; 73/633, 640
See application file for complete search history.

(56) References Cited

U.S. PATENT DOCUMENTS

| | | | |
|---|---|---|---|
| 3,886,490 A | 5/1975 | Green | 340/5 MP |
| 3,955,561 A | 5/1976 | Eggleton | 128/2.05 |
| 3,974,826 A | 8/1976 | Eggleton et al. | |
| 4,034,744 A | 7/1977 | Goldberg | |
| 4,065,976 A | 1/1978 | Taenzer et al. | 73/633 |
| 4,092,867 A | 6/1978 | Matzuk | 73/609 |
| 4,141,347 A | 2/1979 | Green et al. | |
| 4,276,491 A | 6/1981 | Daniel | 310/317 |
| 4,282,755 A | 8/1981 | Gardineer et al. | 73/634 |
| 4,375,818 A * | 3/1983 | Suwaki et al. | 600/463 |
| 4,399,703 A | 8/1983 | Matzuk | 73/621 |
| 4,407,293 A | 10/1983 | Suarez, Jr. et al. | 128/660 |
| 4,412,147 A | 10/1983 | Nagura et al. | |
| 4,421,118 A | 12/1983 | Dow et al. | 128/660 |
| 4,424,813 A | 1/1984 | Havlice et al. | 128/660 |
| 4,431,007 A | 2/1984 | Amazeen et al. | 128/660 |
| 4,489,729 A | 12/1984 | Sorenson et al. | |

(Continued)

FOREIGN PATENT DOCUMENTS

| | | |
|---|---|---|
| EP | 0727963 B1 | 6/2005 |
| WO | WO 94/27501 | 12/1994 |
| WO | WO 2004/007098 A1 | 1/2004 |

OTHER PUBLICATIONS

Gniadecka, M., et al., "Age-related diurnal changes of dermal oedeme: evaluation by high-frequency ultrasound," *Brit Jour of Derm* 131:849-855 (1994).

(Continued)

*Primary Examiner*—Francis J. Jaworski
(74) *Attorney, Agent, or Firm*—Needle & Rosenberg, P.C.

(57) ABSTRACT

A system for producing an ultrasound image comprises a scan head having a transducer capable of generating ultrasound energy at a frequency of at least 20 megahertz (MHz), and a processor for receiving ultrasound energy and for generating an ultrasound image at a frame rate of at least 15 frames per second (fps).

55 Claims, 21 Drawing Sheets

U.S. PATENT DOCUMENTS

| | | | |
|---|---|---|---|
| 4,524,623 A | 6/1985 | Terwilliger | 73/633 |
| 4,546,771 A | 10/1985 | Eggleton et al. | |
| 4,612,937 A | 9/1986 | Miller | |
| 4,649,925 A | 3/1987 | Dow et al. | 128/660 |
| 4,664,123 A | 5/1987 | Iinuma | |
| 4,722,346 A | 2/1988 | Chen | 128/660 |
| 4,796,632 A | 1/1989 | Boyd et al. | 128/662 |
| 4,867,169 A | 9/1989 | Machida et al. | 128/662 |
| 5,099,847 A | 3/1992 | Powers et al. | |
| 5,105,814 A | 4/1992 | Drukarey et al. | |
| 5,119,342 A | 6/1992 | Harrison, Jr. et al. | |
| 5,161,536 A | 11/1992 | Vilkomerson et al. | |
| 5,192,549 A | 3/1993 | Barenoiz et al. | |
| 5,278,757 A | 1/1994 | Hoctor et al. | |
| 5,313,949 A | 5/1994 | Yock | |
| 5,313,950 A | 5/1994 | Ishikawa et al. | |
| 5,318,033 A | 6/1994 | Savord | |
| 5,329,194 A * | 7/1994 | Dow et al. | 310/17 |
| 5,357,963 A * | 10/1994 | Mayol et al. | 600/446 |
| 5,379,642 A | 1/1995 | Reckwerdt et al. | |
| 5,379,772 A * | 1/1995 | Imran | 600/463 |
| 5,412,854 A * | 5/1995 | Lockwood et al. | 29/25.35 |
| 5,456,256 A | 10/1995 | Schneider et al. | 128/660.09 |
| 5,474,074 A | 12/1995 | Suorsa et al. | |
| 5,485,845 A | 1/1996 | Verdonk et al. | |
| 5,488,954 A | 2/1996 | Sleva et al. | |
| 5,505,088 A | 4/1996 | Chandraranta | 73/623 |
| 5,513,640 A | 5/1996 | Yamazaki et al. | |
| 5,524,623 A | 6/1996 | Liu | |
| 5,588,434 A | 12/1996 | Fujimoto | |
| 5,588,435 A | 12/1996 | Weng et al. | |
| 5,615,680 A | 4/1997 | Sano | |
| 5,629,865 A | 5/1997 | Roth | 364/508 |
| 5,636,632 A | 6/1997 | Bommannan et al. | |
| 5,647,364 A | 7/1997 | Schneider et al. | 128/660.09 |
| 5,651,366 A | 7/1997 | Liang et al. | |
| 5,655,537 A | 8/1997 | Crowley | |
| 5,678,552 A | 10/1997 | Savord | |
| 5,690,110 A | 11/1997 | Tanaka | |
| 5,724,312 A | 3/1998 | Oppelt | |
| 5,776,068 A | 7/1998 | Silverman et al. | |
| 5,792,058 A | 8/1998 | Lee et al. | |
| 5,839,442 A | 11/1998 | Chiang et al. | |
| 5,844,140 A | 12/1998 | Seale | |
| 5,865,650 A | 2/1999 | Marian, Jr. et al. | |
| 5,879,305 A | 3/1999 | Yock et al. | |
| 5,921,931 A | 7/1999 | O'Donnell et al. | |
| 6,001,062 A | 12/1999 | Masters | 600/443 |
| 6,036,647 A | 3/2000 | Suorsa et al. | |
| 6,042,545 A | 3/2000 | Hossack et al. | |
| 6,055,861 A | 5/2000 | Banta, Jr. et al. | |
| 6,063,030 A | 5/2000 | Vara et al. | |
| 6,064,628 A | 5/2000 | Uhlendorf et al. | 367/7 |
| 6,066,099 A | 5/2000 | Thomenius et al. | |
| 6,073,045 A | 6/2000 | Dyson et al. | 600/433 |
| 6,139,502 A | 10/2000 | Fredriksen | 600/459 |
| 6,152,877 A | 11/2000 | Masters | |
| 6,193,662 B1 | 2/2001 | Hwang | |
| 6,201,900 B1 | 3/2001 | Hossack et al. | |
| 6,221,016 B1 | 4/2001 | Hayakawa | |
| 6,228,030 B1 | 5/2001 | Urbano et al. | |
| 6,228,031 B1 | 5/2001 | Hwang et al. | |
| 6,241,672 B1 | 6/2001 | Hochman et al. | |
| 6,245,017 B1 | 6/2001 | Hashimoto et al. | |
| 6,251,073 B1 | 6/2001 | Imran et al. | |
| 6,261,231 B1 | 7/2001 | Damphousse et al. | 600/437 |
| 6,267,734 B1 | 7/2001 | Ishibashi et al. | |
| 6,312,382 B1 | 11/2001 | Mucci et al. | |
| 6,315,725 B1 | 11/2001 | Masters | 600/443 |
| 6,315,732 B1 | 11/2001 | Suorsa et al. | |
| 6,325,759 B1 | 12/2001 | Pelissier | |
| 6,344,023 B1 | 2/2002 | Fukukita et al. | |
| 6,346,079 B1 | 2/2002 | Haider et al. | |
| 6,360,027 B1 | 3/2002 | Hossack et al. | |
| 6,379,304 B1 | 4/2002 | Gilbert et al. | |
| 6,406,428 B1 | 6/2002 | Mittelstaedt | |
| 6,491,637 B2 | 12/2002 | Foster et al. | 600/452 |
| 6,494,835 B1 | 12/2002 | Ciezki et al. | |
| 6,508,768 B1 | 1/2003 | Hall et al. | |
| 6,511,430 B1 | 1/2003 | Sherar et al. | |
| 6,530,887 B1 | 3/2003 | Gilbert et al. | |
| 6,540,681 B1 | 4/2003 | Cheng et al. | |
| 6,544,187 B2 | 4/2003 | Seward | |
| 6,547,731 B1 | 4/2003 | Coleman et al. | |
| 6,558,326 B2 | 5/2003 | Pelissier | |
| 6,569,102 B2 | 5/2003 | Imran et al. | |
| 6,572,549 B1 | 6/2003 | Jong et al. | |
| 6,574,499 B1 | 6/2003 | Dines et al. | |
| 6,579,122 B1 | 6/2003 | Chen | 439/570 |
| 6,589,174 B1 | 7/2003 | Chopra et al. | |
| 6,629,929 B1 | 10/2003 | Jago et al. | |
| 6,679,845 B2 | 1/2004 | Ritter et al. | |
| 6,837,855 B1 | 1/2005 | Puech | 600/452 |
| 6,923,767 B2 | 8/2005 | Saied et al. | |
| 6,949,071 B1 | 9/2005 | Saied et al. | |
| 2001/0031922 A1 | 10/2001 | Weng et al. | |
| 2002/0007119 A1 | 1/2002 | Pelissier | |
| 2002/0050169 A1 | 5/2002 | Ritter et al. | |
| 2002/0128550 A1 | 9/2002 | Van Den Brink et al. | |
| 2002/0173719 A1 | 11/2002 | Zhao et al. | |
| 2002/0173720 A1 | 11/2002 | Seo et al. | |
| 2003/0088182 A1 | 5/2003 | He et al. | |
| 2003/0097068 A1 | 5/2003 | Hossack et al. | |
| 2003/0100833 A1 | 5/2003 | He et al. | |
| 2003/0114755 A1 | 6/2003 | Jong et al. | |
| 2004/0082858 A1 | 4/2004 | Fukuda | 600/443 |
| 2004/0111026 A1 | 6/2004 | Schoenfeld | |
| 2004/0176789 A1 | 9/2004 | Lee et al. | 606/170 |
| 2004/0193048 A1 | 9/2004 | Tsoref | |
| 2004/0225215 A1 | 11/2004 | Querleux et al. | |
| 2004/0236219 A1 | 11/2004 | Liu et al. | 600/437 |
| 2005/0010111 A1 | 1/2005 | Kristoffersen | |
| 2005/0070796 A1 | 3/2005 | Tsujita | |
| 2005/0124894 A1 | 6/2005 | Puech | 600/450 |
| 2005/0131289 A1 | 6/2005 | Aharoni et al. | |
| 2005/0154287 A1 | 7/2005 | Schluter | |
| 2005/0154305 A1 | 7/2005 | Kamiyama | |
| 2005/0240102 A1 | 10/2005 | Rachlin | 600/437 |

OTHER PUBLICATIONS

Gniadecka, M., et al., "Effects of ageing on dermal echogenicity," *Skin Research and Tech.*, 7:204-207 (2001).

Harland, C.C., et al., "Differentiation of common benign pigmented skin lesions from melanoma by high-resolution ultrasound," *Brit Jour of Derm* 143:1-10 (2000).

Lucassen, G.W., et al., "The effectiveness of massage treatment on cellulite as monitored by ultrasound imaging," *Skin Research and Tech* 3:154-160 (1997).

Seidenari, S., et al., "Ultrasound B scanning with image analysis for assessment of allergic patch test reactions," *Contact Dermatitis* 24:216-222 (1991).

Seidenari, S., et al., "Echographic Evaluation with Image Analysis of Normal Skin: Variations according to Age and Sex," *Skin Pharmacol*, 7:201-209 (1994).

Serup, J., "Ten Years' Experience with High-Frequency Ultrasound Examination of the Skin: Development and Refinement of Technique and Equipment," *Ultrasound in Dermatology*. Berlin: Springer, 41-54 (1992).

Berson et al. "High frequency ultrasonic devices:advantages and applications." European J. Ultrasound 1999; vol. 10:53-63.

Erickson et al. Institute of Electrical and Electronics Engineers: "A hand-held, high frequency ultrasound scanner." 2001, IEEE Ultrasonics Symposium Proceedings, Atlanta, GA; Oct. 7-10, 2001. IEEE Ultrasonics Symposium Proceedings, New York, NY: IEEE, US vol. 2 of 2; Oct. 7, 2001.

Turnbull et al., "In vivo ultrasound biomicroscopy in developmental biology" *Trends in Biotechnology*, 20(8):S29-S33 (2002).

* cited by examiner

HIGH FREQUENCY, HIGH FRAME-RATE ULTRASOUND IMAGING SYSTEM

CROSS-REFERENCE TO RELATED APPLICATIONS

This application claims priority to and the benefit of U.S. Provisional Application No. 60/417,164, entitled "RMV SCANHEAD SYSTEM,", filed on Oct. 10, 2002; U.S. Provisional Application No. 60/468,958, entitled "SCAN HEAD FOR ULTRASOUND IMAGING SYSTEM," filed on May 9, 2003; U.S. Provisional Application No. 60/468, 956, entitled "REMOVABLE ACOUSTIC WINDOW," filed on May 9, 2003; and U.S. Provisional Application No. 60/470,234, entitled "METHOD AND APPRATUS FOR OBTAINING AN ULTRASOUND IMAGE," filed on May 14, 2003, all of which are incorporated in this document by reference.

BACKGROUND

Scanheads that were developed in the late 1970's and early 1980's for imaging human tissue are still useful for many ultrasound imaging applications. A transducer located in the scanhead comprises discs of piezoelectric material, which when excited electrically vibrated at a frequency usually chosen to be between 2 and 10 MHz. At these frequencies, the vibrational energy of the transducer was directional and radiated from two faces of a thin circular disc in reasonably well-defined beams. In general, the energy radiating from the back of the transducer is absorbed by a suitable material while that from the front is coupled to the patient by a fluid capable of transmitting ultrasound energy with low loss characteristics. Emerging through a thin, low-loss cap, the energy is further coupled to the patient with a sonolucent gel applied to the patient's skin. Echoes resulting from the interaction of the ultrasound energy with body tissue traverse the same path in reverse, and when they strike the transducer generate an electrical signal whose strength is a function of the echogenicity of a target within the patient and the target's depth below the patient's skin. The location in depth is determined from the time interval between the transmit pulse and the received echo. With this information and the directional information delivered by a position encoder coupled to the transducer, the scanheads generate a gray-scale image of the tissue lying in a scan plane within the patient, which is refreshed and updated with every sweep of the transducer across the image plane. Two sweeps of the transducer comprises one operating cycle, referred to as 1 Hz, and equates to two frames per second.

Two dimensional ultrasound images (also known as B-scans) are made up of a number of adjacent lines of ultrasound data called A-scans, which are acquired from the scanhead through successive sweeps of the transducer. The line of ultrasound data is acquired when a transducer transmits the ultrasound pulse into the tissue being studied and then receives the ultrasound signal reflected by the tissue along a beam axis of the transducer. The lines of ultrasound data are located within the same plane and are usually spaced at constant intervals. Each line of data is acquired with the ultrasound beam axis moved laterally within the plane by a known incremental distance. The ultrasound image may have a linear format, in which the lines are parallel to one another and equally spaced, or a sector format, in which the lines radiate from an apex with equal angles between them. To produce a linear format image, the transducer is moved laterally, without altering the angle between the transducer and the line along which it is moved. To produce a sector format image, the transducer is mounted to a fixture, which rotates about an apex, causing the transducer to move in an arc. As the transducer moves, the position within the scan plane is tracked so that an associated ultrasound system can display the ultrasound line data at the correct locations within the displayed image.

Early clinical diagnostic ultrasound systems used wobbler scanheads to produce the sector format images. These systems used low frequency ultrasound, in the 2 to 5 MHz range. The wobbler scanheads usually consisted of the transducer located within a fluid filled chamber, a motor, a position encoder, and an acoustic window through which the ultrasound passed. The motor drive mechanism usually moved the transducer through an arc, resulting in a sector scan type image format while the position encoder kept track of the transducer position. The wall of the fluid filled chamber, which faced the tissue being imaged, acted as an acoustic window, which was usually made of a hard plastic material. This window allowed ultrasound to pass through with little attenuation. Further, in general, there is a reflected ultrasound wave which does not pass through the window. This wave can reverberate between the transducer and the window several times before dissipating. The reverb components, which strike the transducer, can cause an undesirable artifact in the ultrasound image. The magnitude of the reflected wave is determined by the acoustic impedance mismatch between the material used for the window and the fluid in the transducer chamber. The amount of attenuation is determined by the window material, which occurs as the ultrasound energy passes through the window. Both attenuation and reflections at the window are undesirable.

In the 80's these mechanically scanned transducers began to be replaced by solid state devices which consist of a plurality of narrow piezoelectric elements which, when excited sequentially, can be used to build up an image. These "linear array" scanheads had been developed at the same time as the mechanical ones, but delivered poorer image quality. Further work, throughout the 80's and 90's resulted in the development of "phased array" scanheads, which have the ability to excite groups of elements in ways that allows electronic beam steering and focusing, which in general produce better images than any mechanical scanhead and at frame rates of 60 frames per second. Today, phased arrays are universally used for ultrasound imaging of human tissue. However, a typical phased array system using a transducer operating at five MHz might have a spatial resolution of 0.5 mm.

One disadvantage with higher operating frequencies is as the operating frequency increases, fabrication difficulties make it challenging to build a phased array type imaging system. As a result, current systems operating in the 30-40 MHz range typically use mechanically scanned single element transducers, in scanheads similar in operating principal to the mechanically scanned systems described above. However, high frequencies generally result in higher attenuation and thus the attenuation due to an acoustic window is increased significantly. Accordingly, current high frequency transducers use a non-encapsulated transducer, which is moved back and forth with a linear servo-motor and position encoder system. At higher frequencies (greater than 30 MHz), transducer encapsulation is impractical due to a breakdown of theoretical properties and characteristics of materials with higher frequencies.

For high frequency transducers, since it is not encapsulated, the moving transducer is exposed. Acoustic coupling to the tissue being imaged is accomplished by creating a mound of ultrasound gel on the surface of the tissue, into which the moving transducer is lowered. Satisfactory imaging depends on the existence of a continuous layer of gel between the transducer and the tissue. If the transducer loses contact with the gel, or if an air bubble forms on the surface of the transducer, imaging will be compromised or even impossible. This type of imaging is restricted to relatively low frame rates, because a rapidly moving transducer will disrupt the gel layer and is more likely to lose contact. Further disadvantages of exposed transducers are that they can create a hazard to delicate tissue, and can also expose the transducer to possible damage from impact.

A further disadvantage in mechanical ultrasound scanheads is the use of moving magnet motors. The attraction of the moving magnet type is that there is no need for flexible wires to deliver power to the drive coil because the drive coil is stationary and the permanent magnet is attached to the moving member or rotor. Furthermore, the magnet type motor is inefficient. The usual mechanical scanhead consumes up to three Watts of electrical power, which is converted into heat that must be dissipated through plastic walls of the scanhead housing. As the housing is generally a poor conductor of heat the internal temperature of the scanhead may rise, which in time can degrade materials, alter the acoustic properties of the device, and can even be uncomfortable to the subject. Another reason the magnet motor is inefficient is that in an effort to keep the oscillating mass low, the moving magnets are kept relatively small. To achieve a certain torque, motor currents are correspondingly high, which gives rise to a high $I^2R$ loss. These losses increase roughly as the square of the scanning rate.

SUMMARY

In one embodiment, the high-frequency, high frame-rate ultrasound imaging system comprises a scan head having a transducer capable of generating ultrasound energy at a frequency of at least 20 megahertz (MHz), and a processor for receiving ultrasound energy and for generating an ultrasound image at a frame rate of at least 15 frames per second (fps).

Related methods of operation are also provided. Other systems, methods, features, and advantages of the high-frequency, high frame-rate ultrasound imaging system will be or become apparent to one with skill in the art upon examination of the following figures and detailed description. It is intended that all such additional systems, methods, features, and advantages be included within this description, be within the scope of the high-frequency, high frame-rate ultrasound imaging system, and be protected by the accompanying claims.

BRIEF DESCRIPTION OF THE FIGURES

The high-frequency, high frame-rate ultrasound imaging system can be better understood with reference to the following figures. The components within the figures are not necessarily to scale, emphasis instead being placed upon clearly illustrating the principles of the high-frequency, high frame-rate ultrasound imaging system. Moreover, in the figures, like reference numerals designate corresponding parts throughout the different views.

FIG. 7 provides further details of the scanhead of FIG. 3A.

DETAILED DESCRIPTION

Figure 1A:
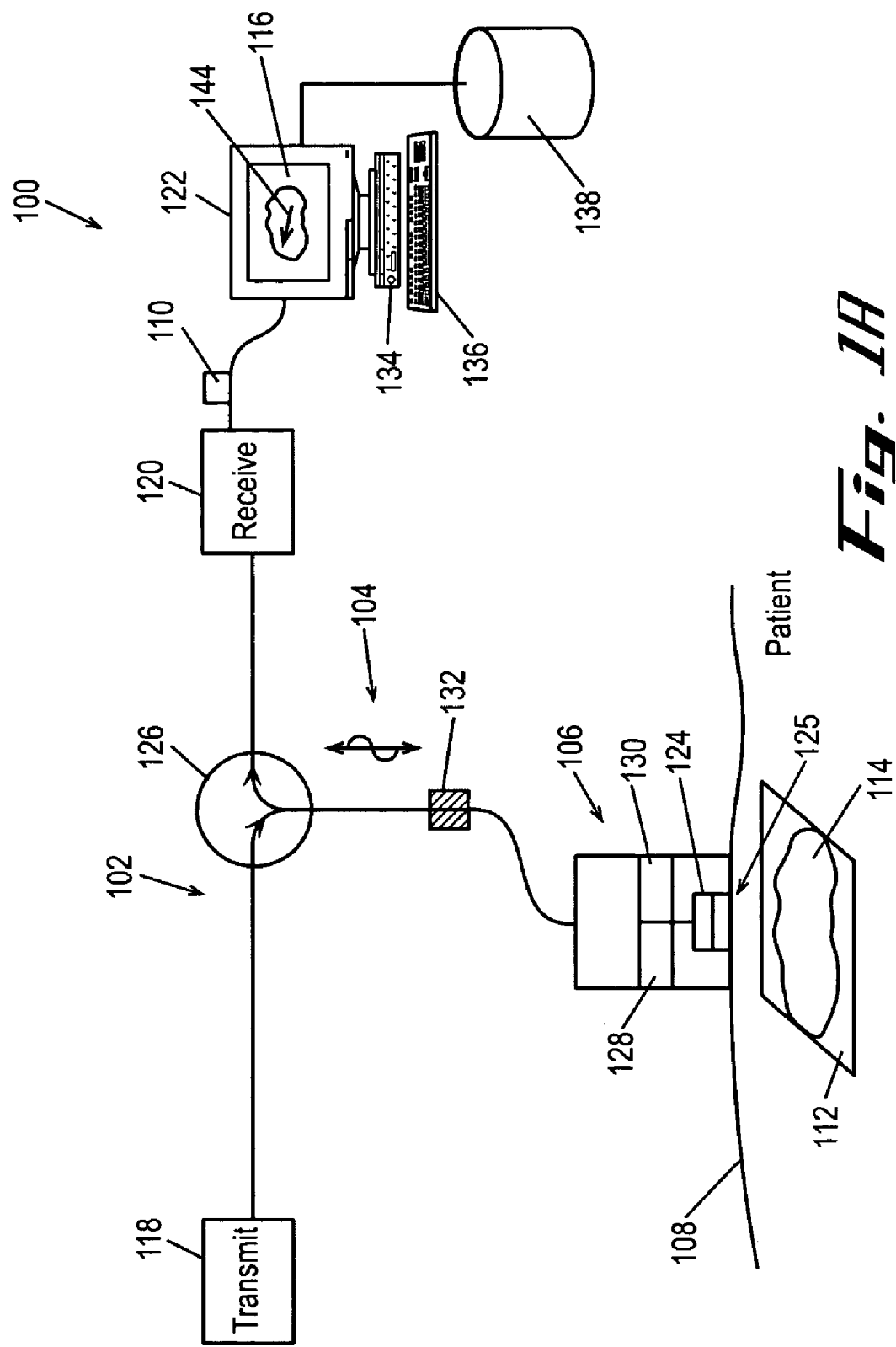
FIG. 1A is a diagram of one embodiment of a scanhead system.

Referring to FIG. 1A, an ultrasound scanning system 100 has an electronics circuit 102 for transmitting and receiving a series of ultrasound pulses 104 to and from a probe or scanhead 106. The scanhead 106 can be situated on a subject 108 to record image data 110 of a scan plane 112, representing a cross section of a target 114 for display on a display 116. The target 114 may be, for example, the organ of a small animal, such as a mouse, a rat or another research subject. Examples of organs that can be imaged include, but are not limited to, a lung, a heart, a brain, a kidney, a liver and blood flowing within the subject. Further, the ultrasound imaging system can be used to image a neo-plastic condition. The circuit 102 has a transmit subsystem 118 for generating the pulses 104 and a receive subsystem 120 for receiving the corresponding echo pulses 104, which are directed to a computer 122 for processing and eventual display as the image scan data 110. The scanhead 106 is coupled at 126 to the circuit 102. The scanhead 106 has a transducer assembly 124, with a membrane 125, which is coupled to a position encoder 128 in conjunction with a torque motor 130. The encoder 128 and motor 130 monitor the position of the transducer assembly 124 within the scanhead 106. The corresponding position data 132 is transmitted with the pulses 104, representing the image data 110, to the computer 122. The scanhead 106 can be used as an encapsulated real-time probe for recording and displaying image data 110 obtained in real-time at high frequencies, such as but not limited to greater than 20 MHz and including 25 MHz, 30 MHz, 35 MHz, 40 MHz, 45 MHz, 50 MHz, 55 MHz, 60 MHz and higher. Further, transducer operating frequencies significantly greater than those mentioned above are also contemplated.

Referring again to FIG. 1A, the system 100 also includes a system processor 134. The processor 134 is coupled to the display or monitor 116 and to a human-machine interface 136, such as a keyboard, mouse, or other suitable device. If the monitor 116 is touch sensitive, then the monitor 116 can be employed as the input element for the human-machine interface 136. A computer readable storage medium 138 is coupled to the processor 134 for providing instructions to the processor 134 to instruct and/or configure the operation of the monitor 116 for recording and displaying the data 110, 132 on the monitor 116. The computer readable medium 138 can include hardware and/or software such as, by way of example only, magnetic disks, magnetic tape, optically readable medium such as CD ROM's, and semi-conductor memory such as PCMCIA cards. In each case, the medium 138 may take the form of a portable item such as a small disk, floppy diskette, cassette, or it may take the form of a relatively large or immobile item such as hard disk drive, solid state memory card, or RAM coupled to the processor 134. It should be noted that the above listed example mediums 138 can be used either alone or in combination.

Figure 1B:
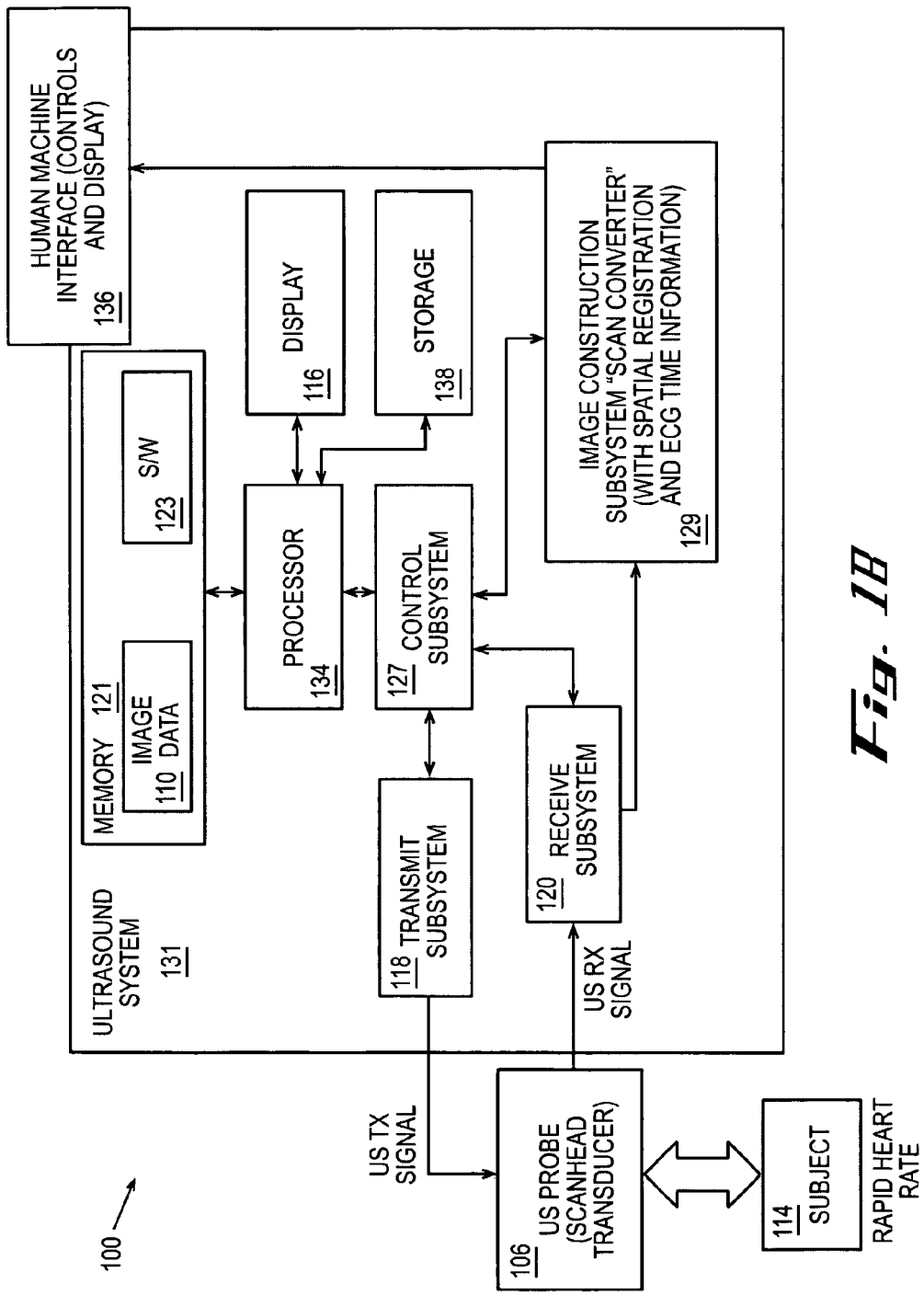
FIG. 1B is a block diagram illustrating the ultrasound imaging system of FIG. 1A.

FIG. 1B is a block diagram illustrating the ultrasound imaging system 100 of FIG. 1A. The system 100 operates on a subject 114. The ultrasound probe 106 can be placed in proximity to the subject 114 to obtain image information.

The ultrasound system 131 includes a control subsystem 127, a scan converter 129, the transmit subsystem 118, the receive subsystem 120 and the user input device 136. The processor 134 is coupled to the control subsystem 127 and the display 116 is coupled to the processor 134. A memory 121 is coupled to the processor 134. The memory 121 can be any type of computer memory, and is typically referred to as random access memory "RAM," in which the software 123 of the high-frequency, high frame-rate ultrasound imaging system executes.

The high-frequency, high frame-rate ultrasound imaging system can be implemented using a combination of hardware and software. The hardware implementation of the high frequency, high frame-rate ultrasound imaging system can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc.

The software for the high frequency, high frame-rate ultrasound imaging system comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM), a read-only memory (ROM), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

The memory 121 also includes the image data obtained by the ultrasound system 100. A computer readable storage medium 138 is coupled to the processor for providing instructions to the processor to instruct and/or configure processor to perform steps or algorithms related to the operation of the ultrasound system 131, as further explained below. The computer readable medium can include hardware and/or software such as, by way of example only, magnetic disks, magnetic tape, optically readable medium such as CD ROM's, and semiconductor memory such as PCMCIA cards. In each case, the medium may take the form of a portable item such as a small disk, floppy diskette, cassette, or it may take the form of a relatively large or immobile item such as hard disk drive, solid state memory card, or RAM provided in the support system. It should be noted that the above listed example mediums can be used either alone or in combination.

The ultrasound system 131 includes a control subsystem 127 to direct operation of various components of the ultrasound system 131. The control subsystem 127 and related components may be provided as software for instructing a general purpose processor or as specialized electronics in a hardware implementation. The ultrasound system 131 includes a scan converter 129 for converting the electrical signals generated by the received ultrasound echoes to data that can be manipulated by the processor 134 and that can be rendered into an image on the display 116. The control subsystem 127 is connected to a transmit subsystem 118 to provide an ultrasound transmit signal to the ultrasound probe 106. The ultrasound probe 106 in turn provides an ultrasound receive signal to a receive subsystem 120. The receive subsystem 120 also provides signals representative of the received signals to the scan converter 129. The receive subsystem 120 is also connected to the control subsystem 127. The scan converter 32 is directed by the control subsystem 127 to operate on the received data to render an image for display using the image data 110.

The ultrasound system 131 transmits and receives ultrasound data through the ultrasound probe 106, provides an interface to a user to control the operational parameters of the imaging system 100, and processes data appropriate to formulate still and moving images that represent anatomy and/or physiology. Images are presented to the user through the interface display 116.

The human-machine interface 136 of the ultrasound system 131 takes input from the user, and translates such input to control the operation of the ultrasound probe 106. The human-machine interface 136 also presents processed images and data to the user through the display 116.

Figure 2:
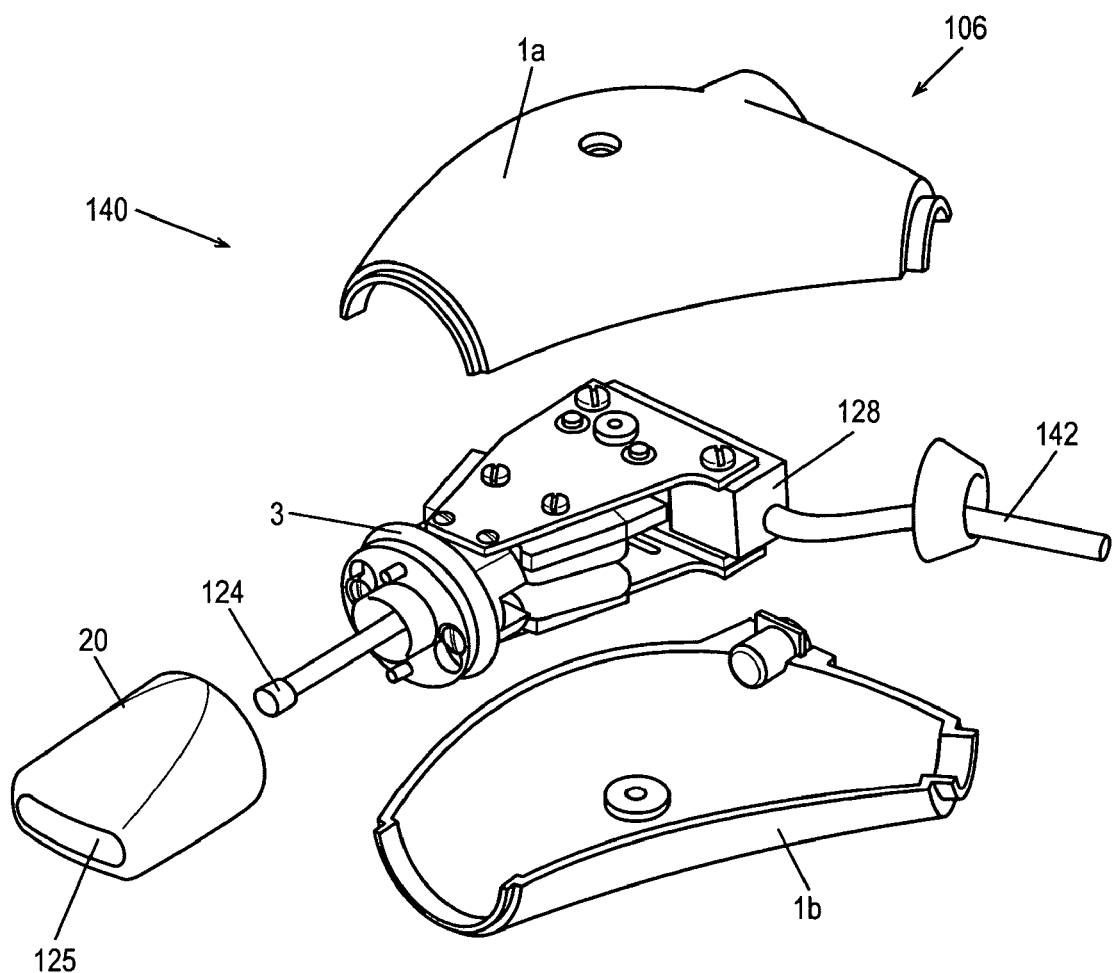
FIG. 2 is a perspective view of a scanhead of the system of FIG. 1.

Referring to FIG. 2, a frame 140 of the scanhead 106 consists of two side plates 1*a* and 1*b*, which are attached to a position encoder 128 at a proximal end and to a pivot frame 3 at a distal end. The position encoder 128 may be, for example, an optical encoder such as a Renishaw RGB25. A nosepiece 20 can be releasably attached to the distal end of the scanhead 106. The side plates 1*a* and 1*b* provide a housing to allow for both hand held scanning and fixtured scanning with the scanhead 106. In addition, the housing provides a strain relieved entry/exit point for cables 142 to and from the scanhead 106. The housing may include an RF shielding component.

Referring to FIGS. 3A, 3B, 4 and 5 a pair of ball bearings 4 are positioned in the pivot frame 3 to locate a rotor assembly 5, which allows the transducer assembly 124 to pivot freely back and forth through an angle of approximately 20 degrees. The rotor assembly 5 comprises a pivot tube 6 to which is connected a yoke 7. Screws through the pivot bearings 4 secure them to the yoke 7. A transducer 8 of the assembly 124 is connected to the distal end of the pivot tube 6, and its' coaxial signal cable 8*a* extends through the pivot tube 6 and out through a slot 6*a*, and is affixed to a circuit board 23 of the circuit 102 (see FIG. 1A). At the proximal end of the rotor assembly 5, a lightweight yet stiff paddle 9 supports a rotor coil 10*a* and 10*b*, an encoder code track 12 and a Hall sensor magnet 13. A flexible coax cable 14 leads from the rotor assembly 5 from the side opposite the transducer coax 8*a*. Both of these are arranged to flex freely without binding or touching other structures as the transducer assembly 124 oscillates back and forth within the scanhead 106. Overall is fitted a plastic housing 31 and 31*a*. A mount nut 32 is secured between the two housing halves 31, 31*a* on assembly. The mount nut 32 has a threaded hole by which the scanhead 106 can be attached to a support arm (not shown), if desired.

Figure 3A:
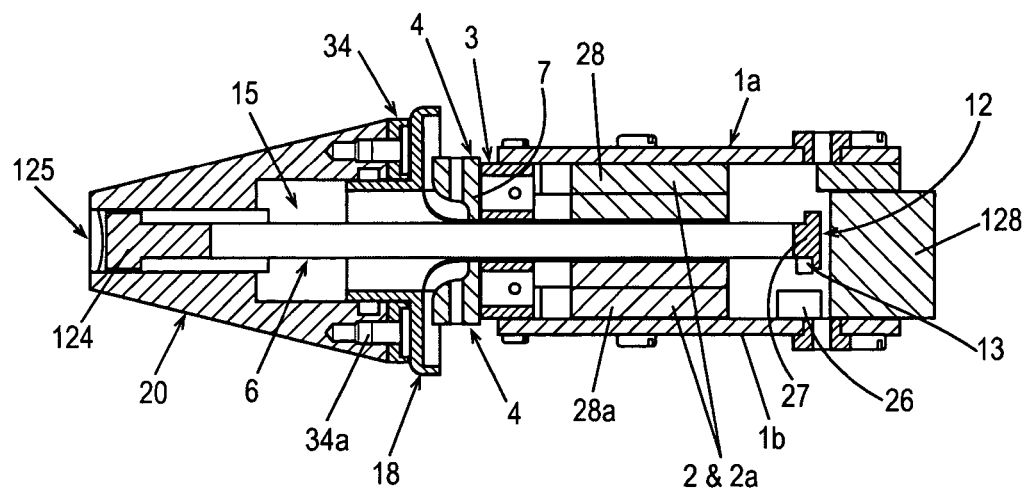
FIG. 3A is a side vide of the scanhead of FIG. 2.
Figure 3B:
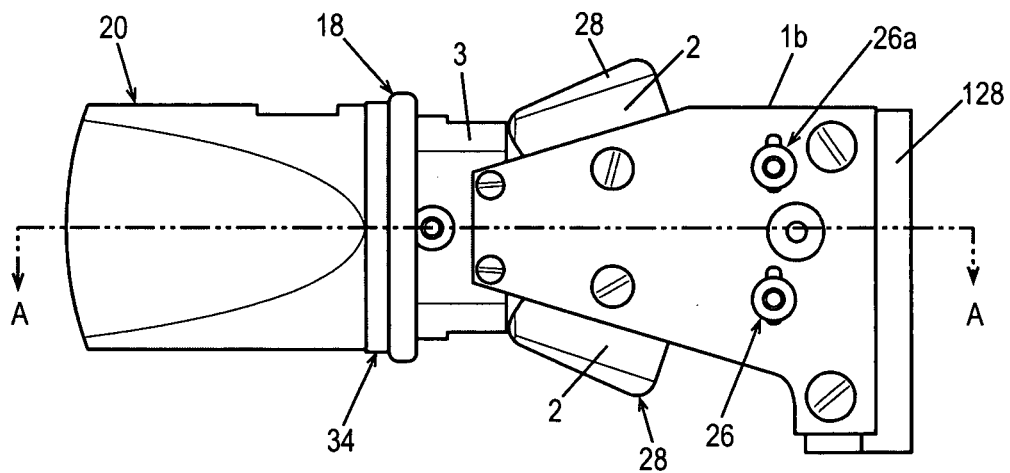
FIG. 3B is a top view of the scanhead of FIG. 2.
Figure 4:
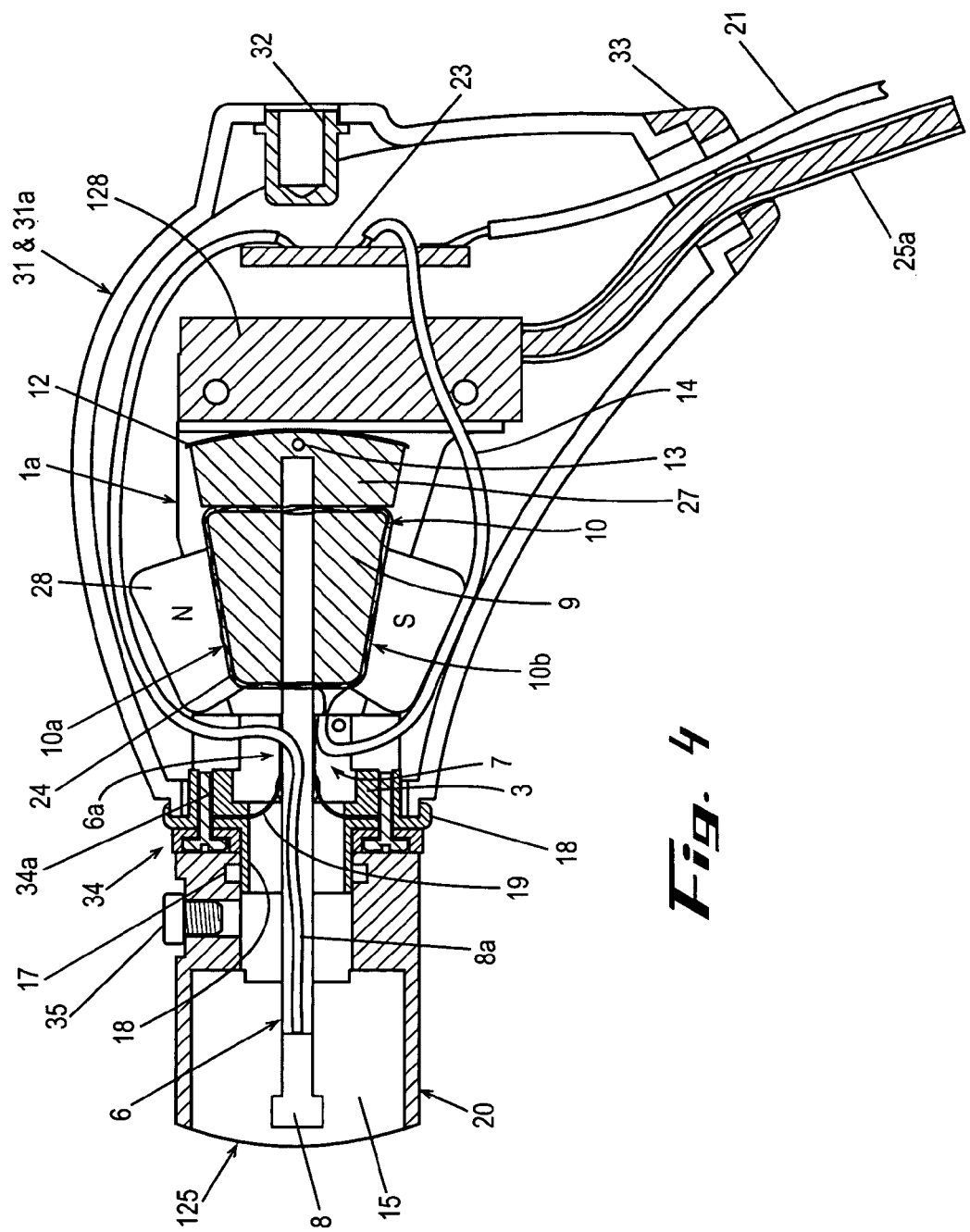
FIG. 4 is section A-A view of the scanhead of FIG. 3B.

Further referring to FIGS. 3A, 3B and 4, the nosepiece 20 is filled with an acoustic coupling fluid 15. The distal end of the scanhead 106 is sealed by the acoustic window 125, which comprises acoustically transparent plastic film and which will be described in further detail below. An o-ring 17 creates a seal between the nosepiece 20 and the nose 18 of the pivot frame 3. A rubber seal diaphragm 19 is located between the nose 18 and the pivot frame 3 making a fluid tight seal. Another fluid tight seal is created between the seal diaphragm and the pivot tube 6 because a hole for the pivot tube 6 in the seal diaphragm 19 is smaller than the pivot tube, creating a tight seal when the seal diaphragm 19 is placed over the pivot tube 6 during assembly. During operation, the seal diaphragm 19 flexes to allow the pivot tube 6 to oscillate back and forth while maintaining the fluid seal there-between. To reduce the degree of flexing of the seal diaphragm 19, it contacts the pivot tube 6 approximately at its pivot point. The yoke 7 straddles this point to clear the seal diaphragm 19. A locking plate 34, comprising, for example, a bayonet-type locking mechanism is located on the back of the nosepiece 20. When the nosepiece 20 is placed over the nose 18, the heads of two screws 34*a* pass through holes in the locking plate 34. A twist of approximately 10 degrees in one direction causes the shank of screws 34*a* to travel in short curved slots in the locking plate 34, trapping the heads of screws 34*a* as shown and locking the nosepiece 20 to the scanhead pivot frame 3. It is noted that the nosepiece 20 can be removed by simply reversing this action. A fill port 35 can be used to initially fill a hollow cavity 15 in nosepiece 20 with acoustic fluid, and to periodically access the cavity 15 to remove any bubbles that may appear.

Referring again to FIGS. 3A, 3B and 4, the transducer assembly 124 is attached to the distal end of the pivot tube 6, creating a fluid tight seal. When in motion, the distal face of the transducer 8 remains a fixed distance (such as, but not limited to, between 0.5 mm to 1 mm) from the acoustic window 125. The coaxial electrical cable 8*a*, carrying signals to and from the transducer 8, leads down the center of the pivot tube 6 and emerges through the slot 6*a* near the pivot axis, thus minimizing motion of the coax cable 8*a*. A slack length of coax cable 8*a* absorbs relative motion during operation, situated between the slot 6*a* and its termination point at the proximal end, i.e. the small printed wiring board (PWB) 23. To this end, the coax cable 8*a* and the coax cable 14 are constructed to have a long flex life. For example, the cables 8*a* and 14 may be constructed using a small diameter (approx. 1 mm), and fine conductors, thereby enhancing flexibility. The PWB 23 contains a pre-amplifier for signals coming from the transducer 8, and acts as a termination point for the signal, power and ground wires from the two Hall sensors 13. The PWB 23 also receives wires 21 entering the scanhead 106 through a cable cap 33 and an encoder cable 25*a*.

Figure 6:
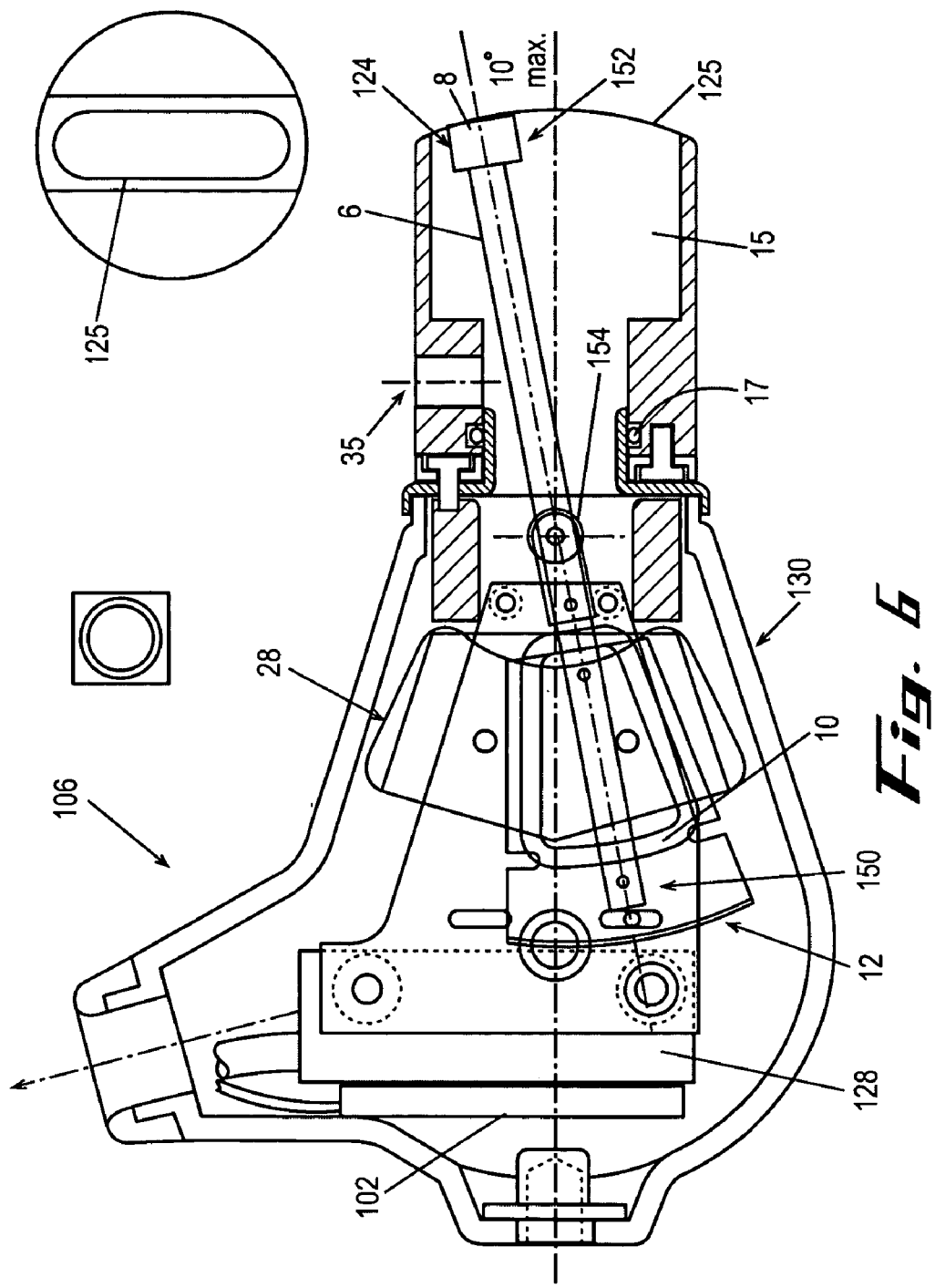
FIG. 6 provides further details of the scanhead of FIG. 4.

Referring to FIGS. 3A, 3B, and 4 rotor windings 10*a* and 10*b*, also shown combined in FIG. 6 as numeral 10, an encoder code track 12 and the Hall sensor actuating magnets 13 are all bonded to the proximal end of the pivot tube 6. An intermediate support structure 27 can be made of rigid polyethylene foam sandwiched between, for example, thin (0.1 mm) epoxy-glass board, forming a lightweight but rigid core to support the rotor windings 24 and the encoder code track 12, in particular.

Referring to FIG. 3B and FIG. 4, the backing iron plates 2 and 2*a* are attached on the inside face of the side plates 1*a* and 1*b*. Field magnets 28 and 28*a* are bonded to the backing iron plates 2 and 2*a*, respectively. The field magnets 28 and 28*a* are magnetized through their thin direction, normal to their facing sides. Each magnet 28, 28*a* has four poles; half of each face is a north pole and the other half is a south pole. The rotor assembly 5 moves back and forth in the gap between the two magnets 28, 28*a*. The south pole of magnet 28 faces the north pole across the gap of magnet 28*a*. The north pole of magnet 28 faces the south pole of magnet 28*a*. There are two pole gaps between the facing magnets 28, 28*a*, polarized in opposite directions. A portion 10*a* of the rotor coil 10 is constrained to oscillate within the confines of one pole gap, and another portion 10*b* oscillates in the other gap.

Figure 5:
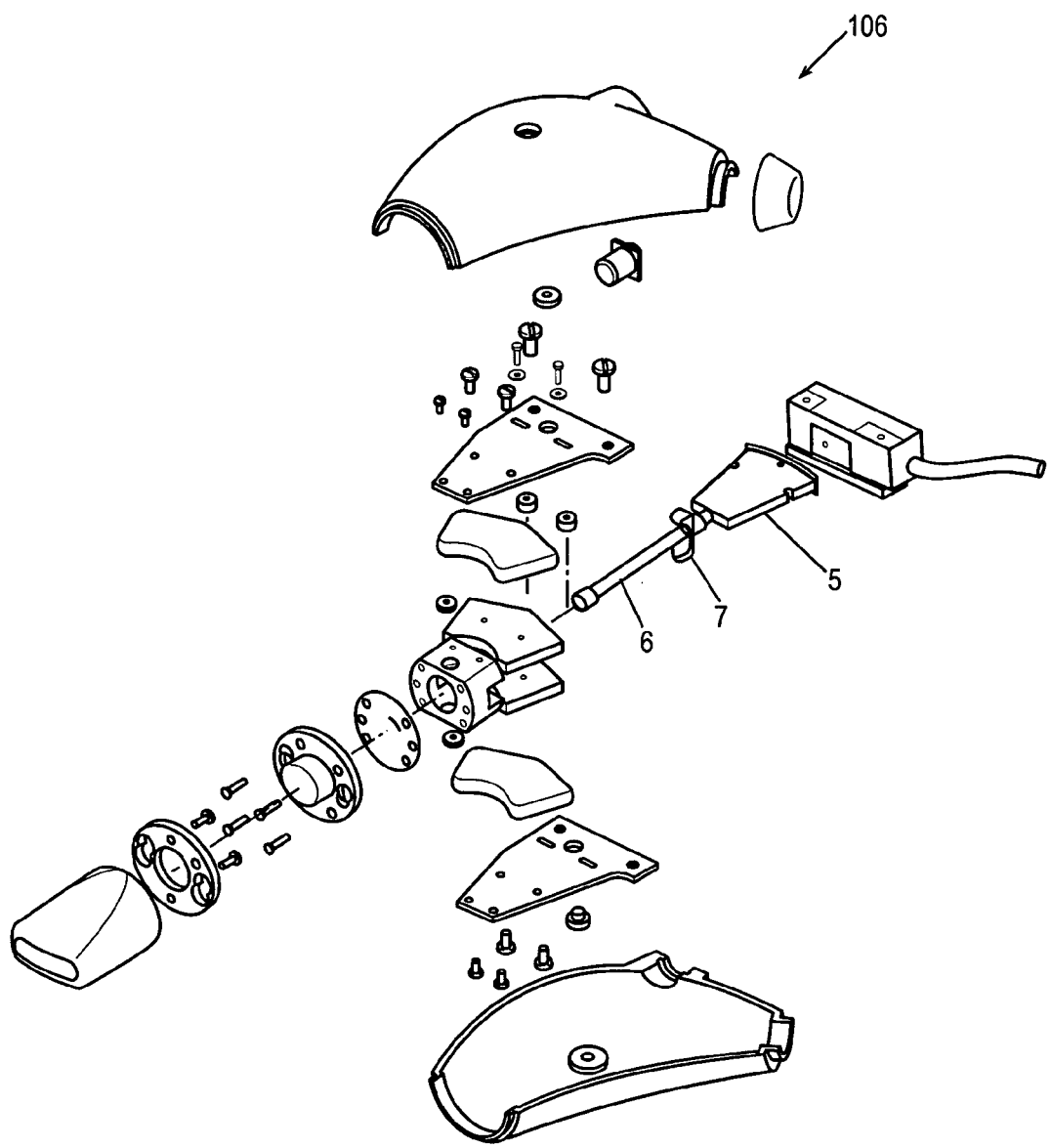
FIG. 5 is a detailed schematic view illustrating the scan head of FIGS. 3A, 3B and 4.

Referring to FIG. 5, an exploded view of the scanhead 106 including the rotor assembly 5, is shown.

Referring to FIG. 6, the torque motor 130 rotates the tube or support arm 6 on the pivot back and forth through a limited angle, i.e. approximately 10-14 degrees. The transducer assembly 124 is connected to one end of the support arm 6, and the position encoder code track 12 is connected to the other end. The transducer 8 of the assembly 124 is aimed such that a focused ultrasound beam can be directed along the longitudinal axis of the pivot tube 6, away from the pivot point. The case and nosepiece 20 surround the torque motor 130, position encoder 128 and transducer 8 such that the transducer 8 is located within the nosepiece section 20. The nosepiece section 20 can be filled with water (or another medium suitable for conducting ultrasound); the torque motor 130 and position encoder 128 are dry due to the seal 19. The pivot tube 6 passes through the flexible seal 19, enabling the pivot tube 6 to move back and forth. The acoustic window 125 can be located at the end of the nosepiece 20.

The position encoder 128 used in the scanhead 106 is, for example, an optical encoder capable of 1 micron (µm) resolution. The position encoder 128 works in conjunction with a reticulated tape strip referred to herein as the encoder code track 12. The position encoder 128 makes use of an optical sensor to count the passage of reticules on the encoder code track 12 as they pass a sensor associated with the position encoder 128. The sensor can sense both direction of travel of the proximal end 150 of the pivot tube 6, and track the position of the travel of the distal end 152 of the pivot tube 6 to within 1 micron.

Referring again to FIG. 6, the encoder code track 12 can be connected to the rear of the pivot tube 6 of the scanhead 106 at a known radial distance from the pivot point 154 of the pivot tube 6. The encoder code track 12 is attached to a precise surface having a radius such that the encoder code track 12 is everywhere tangential to a chord traced out by the pivot tube 6. As the pivot tube 6 pivots, the encoder code track 12 passes back and forth under the optical sensor in the position encoder 128. The result is the digitization of the position of the distal end 152 of the pivot tube 6 at the radius at which the encoder code track 12 is fixed. The position information can be used to determine the location of the transducer 8 located the same radial distance from the pivot point on the other end of the pivot tube 6. Dissimilar distances of the proximal end 150 and distal end 152 measured from the pivot point 154 can also be used, if desired. The optical coupling between the position encoder 128 and the proximal end 150 of the pivot tube 6 reduces the transmission of electronic noise generated by the position encoder 128 and the circuit 102 from the transducer 8.

The transducer 8 can be a high-frequency single-element focused piezoelectric ultrasonic transducer, with a frequency greater than 30 MHz and can be around 40 MHz. The transducer 8 receives the RF electrical pulse 104 as input and produces an ultrasonic acoustic pulse 104 as output during the transmit phase of operation of the circuit 102 (see FIG. 1A and FIG. 1B). The reverse process is performed during the receive phase such that the input to the transducer 8 is an ultrasonic acoustic pulse 104 which is converted by the transducer 8 into a radio frequency electrical signal, represented by data 110. The transducer 8 used in the scanhead 106 can be a broadband transducer 8 fabricated in such a way to ensure a good acoustic match to the acoustic medium in the cavity 15.

The pivot tube 6 can be an ultra light weight stainless steel tube fixed by the bearing assembly 4 in such a way that it pivots about its midpoint 154. The transducer 8 is connected to one end of the pivot tube 6, while the encoder code track 12 is connected to the other end of the pivot tube 6. The pivot tube 6 houses the coils of the torque motor 130 between the bearing assembly 4 and the encoder code track 12, thus forming an integral part of the torque motor 130. Made of tubing, the pivot tube 6 also acts as a conduit for the transducer coax cable 8a.

Referring to FIG. 7, the pivot axis bearing 4 comprises a pair of ball bearings and an off axis, or offset, clamp 146, which holds the pivot tube 6. The offset clamp 146 allows the pivot point of the pivot tube 6 to remain accessible for the routing of cables 8a and mechanical attachment to and from the pivot tube 6. The bearing 4 can be fabricated with precise bearings and accurately machined components to ensure highly repeatable one axis rotation about the pivot point 154. The offset clamp 146 is connected to the pivot tube 6 at one end and is rotatably attached to the pivot point 154 at the other end through pins 148.

The flexible seal 19 can be attached to the midpoint of the pivot tube 6, and the rear of the nose piece 20 bayonet quick release assembly comprising the locking plate 34 and the two screws 34a. The seal 19 can be made of an elastomer membrane that is fastened so that it forms a fluid tight seal between the pivot tube 6 and the nosepiece 20. The seal 19 separates the fluid filled nosepiece 20 from the remainder of the housing which remains dry.

Two Hall sensors 13 are placed in the housing of the scanhead 106 so that they sense the travel of the pivot tube 6 past their respective sensors 13. The sensors 13 are placed so that they produce a signal at the maximum safe travel of the torque motor 130. The limit switches 13 are also placed symmetrically about the pivot point 154 so that they can be used to home the system to a zero deflection, homed, or normal position.

The hollow cavity 15 in the nose piece 20 can be fluid filled. The nosepiece 20 provides a mounting structure to which the acoustic window 125 can be attached. The nosepiece 20 features a drain/fill screw as a fill port 35 through which fluid may be added or removed from the cavity 15. The nosepiece 20 can contain part of a bayonet style quick release assembly allowing it to be removed and changed quickly without the need for tools, while ensuring a fluid tight seal.

The acoustic window 125 comprises a thin membrane of a material well acoustically matched to the fluid in the cavity 15. The acoustic window 125 can be held in a position so that it remains close to and normal to the face of the transducer 8 over the full extent of transducer travel (approximately 0.5 mm to 1 mm, for example). Material from which to form the acoustic window were initially selected or rejected based on known bulk acoustic properties. The membrane can be chosen to exhibit acoustic impedance in the range of 1.3 to 1.7 megaRayles (MRayles), such as 1.5 megarayles. Mechanical constraints such as the manner in which the membrane is attached affect the acoustic impedance and the resulting suitability for use as the acoustic window 125. Material from which the acoustic window can be fabricated include polyester films ranging in thickness from about 0.9 µm to 4.5 µm, polytetrafluoroethylene (PTFE) in thicknesses of 5 µm, 10 µm, 15 µm, and 25 µm, low density polyethylene (LDPE) in thicknesses of 15 µm, 25 µm, and 50 µm, polycarbonate in a thickness of 2 µm, polypropylene in a thickness of 4 µm, latex elastomer in a thickness of 60 µm, and silicone elastomer in a thickness of 25 µm were tested in a variety of configurations including varying the angle of incidence of the ultrasound beam to the membrane forming the acoustic window 125 from 90 degrees to 110 degrees. These materials and thicknesses were used with transducer frequencies of 30-40 MHz. Thinner membranes could be used as the frequency increases. In addition, the encapsulated coupling fluid can be varied to improve the acoustic match with the membrane of the acoustic window 125. For example, ethylene glycol, triethylene glycol, water, light paraffin oil and various aqueous solutions of glycols can be used. Water as a coupling fluid and a 25 µm thick membrane of LDPE can be used as the membrane for the acoustic window 125. Further, an acoustic window 125 formed of 5 µm thick or 15 µm thick PTFE are provided. In addition, thin silicone elastomer can also be provided for the membrane forming the acoustic window 125. The acoustic window 125 maintains a fluid tight seal between the nosepiece 20 and the outer environment of the scanhead 106. Accordingly, the acoustic window 125 used with a high frequency ultrasound transducer 8 is thin, and can be composed of a material that has an acoustic impedance very close to that of the fluid in the cavity 15.

The electronics circuit 102 provides both a low noise RF preamplifier and a proprietary high fidelity protection circuit to the scanhead 106. The electronics circuit 102 protects sensitive receive instruments in the receive subsystem 120 from the high energy pulse 104 used to drive the transducer 8. The low-noise preamplifier boosts the signal of the transducer 8 with minimal distortion.

Referring again to FIGS. 3A, 3B and 4 during operation of the scanhead 106, when a direct current (DC) voltage signal is applied through the rotor coil 10 through the coax cable 14, the Lorentz forces generated by the currents in rotor coil portion 10*a* and rotor coil portion 10*b* act in the same sense, causing the rotor assembly 5 to rotate either clockwise or anti-clockwise about the pivot bearings 4, depending on the polarity of the applied voltage. When the scanhead 106 is started, a DC voltage signal is applied to the rotor coil 10 to drive the rotor assembly 5 towards one end of its range of motion. Before the rotor assembly 5 reaches the end of travel, the Hall sensor 13 triggers one of two Hall sensor magnets 26 and 26*a*, one at each end of travel fixed to side plates 1*a* and 1*b*. The control subsystem 127 responds by reversing the polarity of the voltage supplied to the rotor, driving the rotor assembly 5 in the opposite direction until the other Hall sensor 13 is triggered. All this time, the position encoder 128 reads the encoder code track 12 and determines the position of the transducer 8 relative to the two end-of-travel events indicated by the Hall sensors 13. The control system can now drive the transducer 8 back and forth over whatever path and velocity profile is programmed into the controller, using the signals from the position encoder 128 for positional feedback.

For example, M-mode and Doppler are two other modes of operation for which the scanhead 106 is suited. For either of these modes, the rotor assembly 5 is electrically driven to a fixed position, usually under operator control using a joystick associated with the human-machine interface 136 for input commands. The operator (not shown) can view an image frozen in time on the display 116, or a series of images, which are periodically updated, and manipulate the direction in which the transducer 8 is pointing. An electronic representation 144 (FIG. 1A) of the direction in which the transducer 8 is pointing can be displayed over the ultrasound image on the display 116, and can be used for visual feedback. For the diagnostic imaging of tissue, the propagation path of ultrasound should be entirely within water or another fluid which has acoustic impedance very close to that of tissue. An air gap, or a material located in the path which creates an acoustic impedance mismatch can cause unwanted reflections, which appear as artifacts in the image on the display 116. Usually a coupling gel, which has acoustic properties very similar to water, can be used between the scanhead 106 and the tissue being imaged.

Further, the torque motor 130 in conjunction with the position encoder 29 and encoder code track 12 run in a closed loop. They act as a servo-motor and are controlled by a motor control system associated with the processor 134 so that the pivot tube 6, which can be fixed in place by the pivot bearings 4, rotates back and forth about the pivot axis 154 in a controlled manner. The transducer 8 can be fixed to the end of the pivot tube 6 opposite the encoder code track 12. The pivot tube 6 moves the transducer 8, which is scanned back and forth within the fluid filled nosepiece 20. The location of the transducer 8 is known at all times to within 1 micron. The transducer 8 transmits and receives ultrasonic information which is received and amplified via the circuit 102, and then sent to the processor 134. Due to the lightweight precision nature of the design, this process can be accomplished at 15 Hz allowing for the production of real-time images for display of the image data 110 on the display 116. Operating the transducer 8 at a frequency of 15 Hz equates to a frame rate of 30 frames per second, as two sweeps of the transducer 8 through its range of motion equates to one Hz. Further, the oscillating frequency of the transducer 8 may be increased to increase the frame rate. Further, depending on the frequency of the ultrasound energy transmitted by the transducer, the ultrasound system 131 provides images having a spatial resolution of less than 30 microns. For example, at a frequency of approximately 25 MHz, the spatial resolution is approximately 75-100 microns. As the transducer frequency increases, the spatial resolution improves. At high transducer frequencies in the range of 40 MHz to 60 MHz, spatial resolution may exceed 30 microns. The high operating frequency of the transducer and the precise mechanical positioning of the transducer with an accuracy of approximately 1 µm allow the ultrasound system 131 to provide real-time ultrasound images having spatial resolution in excess of 30 µm.

Further, the scanhead 106 can be designed for use either by hand or on a fixture. The scanhead 106 can also be used as an immersion style scanner in a water bath or it can be coupled with gel to the tissue to be scanned. In these situations, the membrane of the acoustic window 125 may be removed.

In summary, the scanhead 106 is an electrically driven handheld imaging device that oscillates the ultrasound transducer 8 in a fan-shaped arc while maintaining good acoustic coupling between the transducer 8 and the subject 108 being imaged. The position encoder 128 delivers real-time position information to the controlling system processor 134. As the transducer 8 moves, signals from the position encoder 128 trigger transmit pulses 104 and communicate to the system processor 134 the position at which the resulting data stream 110 collected between those pulses 104 should be displayed in the electronic image that comprises the visual output on the display 116. The scanhead 106 can move the transducer 8 continuously back and forth within a fluid environment over a distance of approximately 10 mm in a controlled manner at a rate up to and exceeding 15 Hz, which corresponds to a frame rate of 30 frames per second. The position encoder 128 in the scanhead 106 can record the position of the transducer 8 in real time with an accuracy of 1 µm, and can position the transducer 8 at an arbitrary location within the scan region to an accuracy of 1 µm. The scanhead 106 includes the acoustic window 125 through which the ultrasound energy can be directed towards the subject 108 being imaged. The acoustic window 125 allows the transmission of high frequency ultrasound with minimum attenuation and/or reflection. The scanhead 106 can be sufficiently compact to be easily hand held, and can achieve positioning accuracy to 1 µm with a 15 Hz mechanical pivoting scanning and positioning system. The acoustic window 125 can be compatible with the transmission of high frequency ultrasound energy, at frequencies in excess of 60 MHz. The scanhead 106 can have image resolution smaller than 30 µm, with an imaged region of approximately 8 mm by 8 mm for the scan plane 112 (see FIG. 1A).

The scanhead 106 uses a single moving part, the pivot tube 6, and a limited angle torque motor 130 of the moving coil type. The torque motor 130 produces large torque force with little current draw because the non-moving field magnets 28 and 28a are relatively large and are made of a high energy product material, such as, but not limited to, neodymium iron-boron, which maintains a very high B field across the rotor windings 24. Another benefit of using a moving coil type motor is that the rotor mass, and rotational inertia, can be minimized, which helps to reduce power consumption and vibration. Small structures within the subject 108 being imaged at 40 MHz or greater are often associated with rapid movement. Therefore, such a design allows for operating speeds of 30 Hz or higher, corresponding to 60 frames per second.

The flex seal 19 (see FIG. 4) isolates the fluid in the cavity 15 from the elements on the opposite side of the flex seal 19. The flex seal 19 can be located near the pivot point 154 of the rotor assembly 5 by using the offset clamp 146 to allow the pivot bearings 4 to straddle the point where the flex seal 19 can be attached to the pivot tube 6, which helps to minimize the stresses on the flex seal 19. The attachment of the flex seal 19 can be accomplished by a simple friction fit between the hole in the flex seal 19 and the pivot tube 6. The flex seal 19 can be made of a polyurethane elastomer possessing high fatigue life.

The portion of the pivot tube 6 immersed in the acoustic fluid, and the transducer 8, which can be wholly immersed, can be designed to be neutrally buoyant. When in motion, neutral buoyancy helps cancel vibration that could otherwise be a consequence of the motion of the transducer 8 and pivot tube 6. In fact, in another embodiment of the present invention, the entire oscillating mechanism on either side of the pivot point 154 can be so adjusted to be neutrally buoyant and operates entirely immersed in the acoustic fluid. This can help to eliminate virtually all vibration that would otherwise be transmitted to the operator and the subject 108.

Further, the nosepiece 20 can be easily removed and replaced by the operator. The simplified removal and replacement of the nosepiece 20 facilitates the replacement of a damaged acoustic window 125 or contaminated acoustic fluid. The fill port can be provided on the side of the nosepiece 20 to initially fill the cavity 15 with acoustic fluid when the nosepiece 20 is installed and to displace any bubbles with additional fluid should they develop with use. A simple bayonet type twist lock can be used to secure the nosepiece 20 to the body of the scanhead 106. If the nosepiece 20 should be sterile, as it might for some uses, it can be disposable. An integral part of such a replaceable nosepiece 20 can be a sterile drape or sheath, made of thin plastic, heat sealed or otherwise attached to the base of the nosepiece 20, which could be an injection molded plastic part. The scanhead 106 can also be operated, if desired, with the acoustic window 125 removed.

Figure 8:
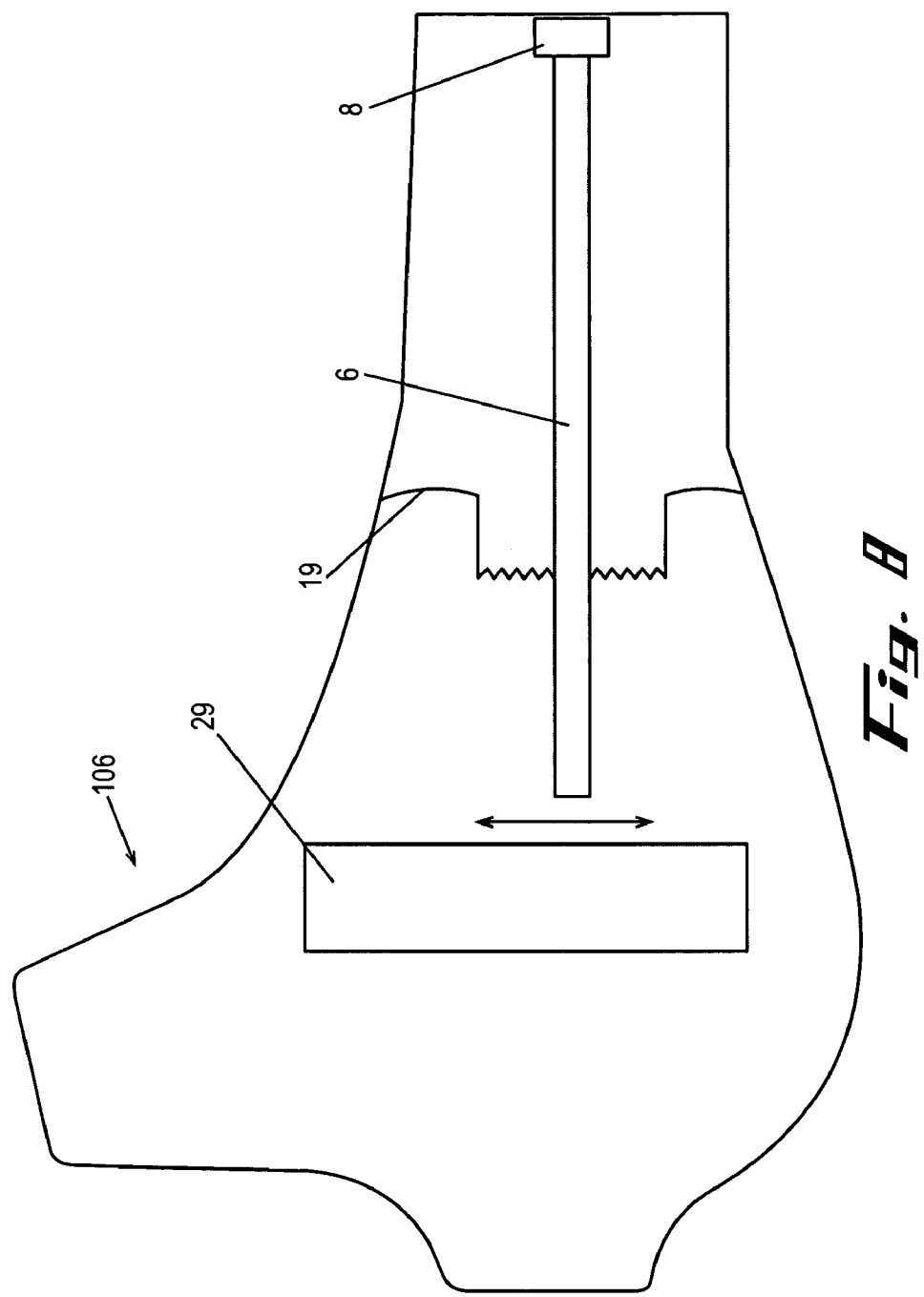
FIG. 8 demonstrates alternative motions of the pivot tube 6.

Referring to FIG. 8, the scanhead 106 can be designed for reciprocal motion of the arm 6 with an appropriate flex seal 19, if desired. The flex seal 19 could be of an accordion design, if desired.

Figure 9:
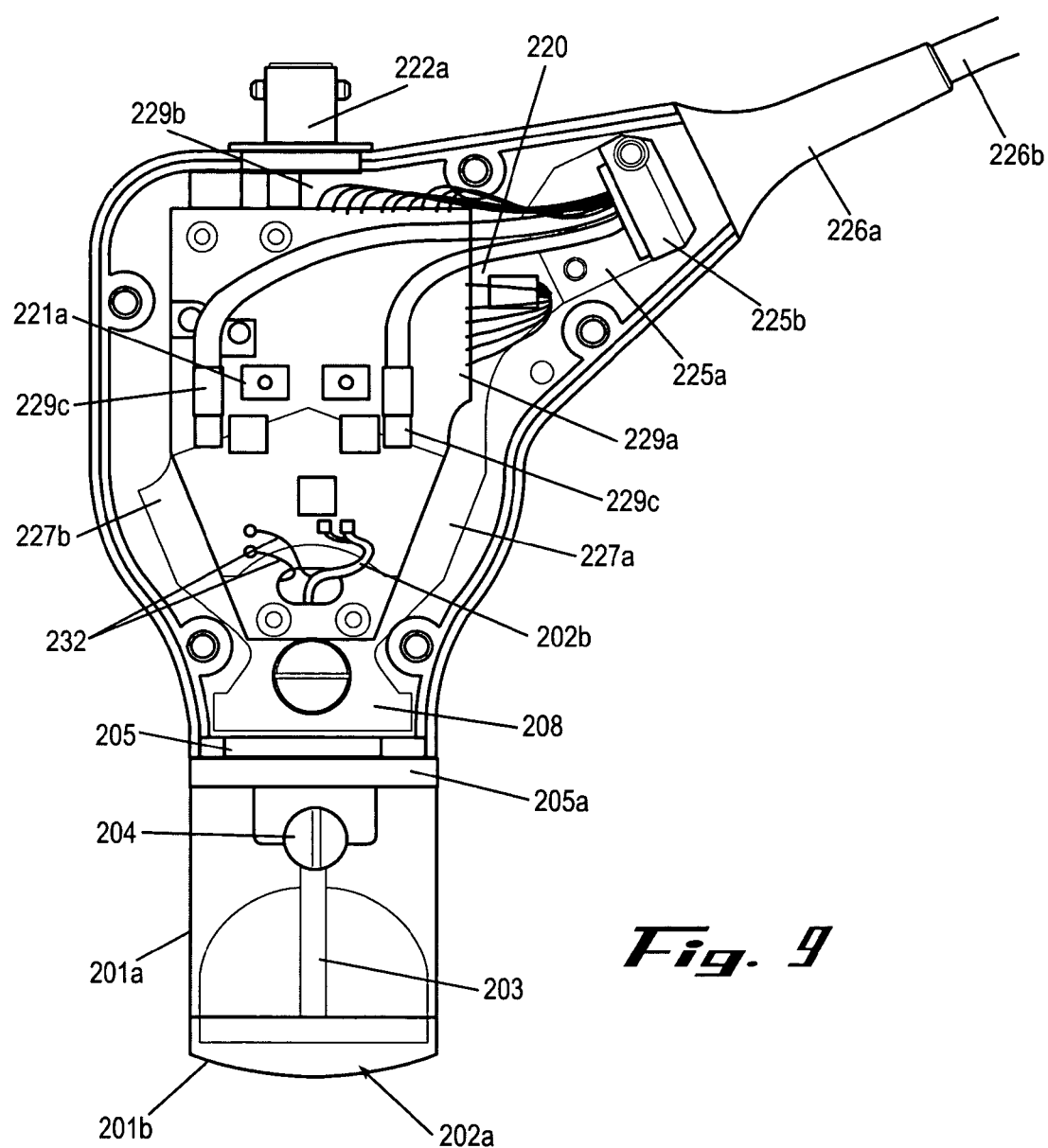
FIG. 9 is a diagram of another embodiment of a scanhead of the system of FIG. 1A.
Figure 10:
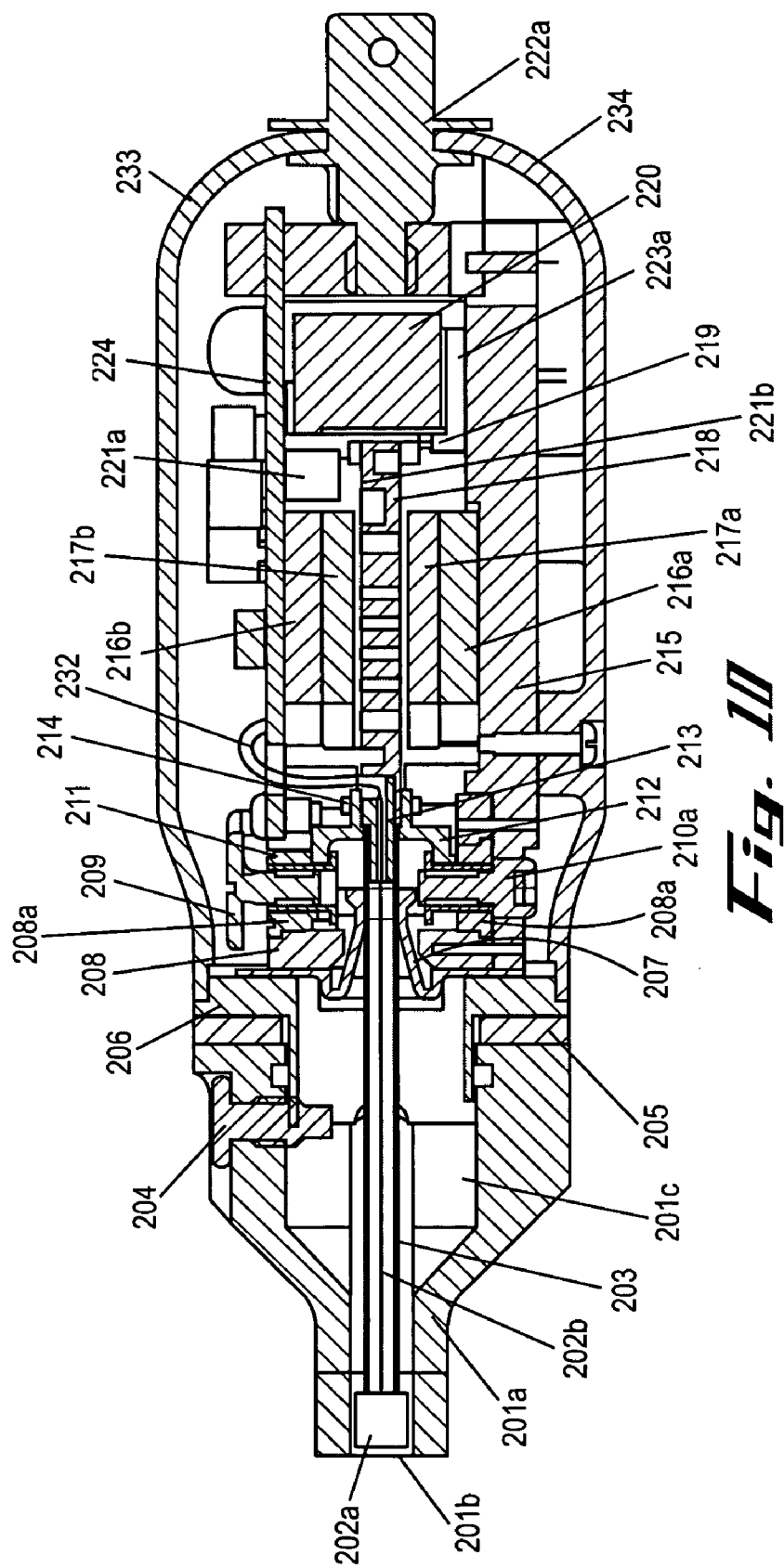
FIG. 10 is a longitudinal cross section of the scanhead of FIG. 9.

Another embodiment of the scanhead 106 is shown in FIGS. 9 and 10. This embodiment of the scanhead, referred to using reference numeral 206, has many components similar in function to components in the previous embodiment, which will be understood from the previous description. The scanhead 206 includes a chassis 215 capable of supporting all of the components of the scanhead 206. A circuit board 224 is integrated into the scan head 206. The chassis 215 supports a strain relief clamp base 225a, a strain relief clamp 225b and a strain relief 226a for securely holding a cable assembly 226b at a proximal end of the chassis 215. The cable assembly 226b connects to electrical connectors 229a, 229b on the circuit board 224. The circuit board 224 includes a motor control element, position monitoring circuit and communicates RF signals between the transducer and the processing elements in the ultrasound system 131 (see FIG. 1B).

The chassis 215 supports a pivot frame 208 that in turn supports a yolk 212 attached to armature 240 (FIG. 11) at a distal end of the chassis 215. The armature 240 is described in further detail below with reference to FIG. 11.

A bayonet style lock plate 205a interfaces with a fixture on a nose 205 that is mounted to the pivot frame 208. The lock plate 205a is attached to a removable nosepiece 201a. The nosepiece 201a has an acoustic window including a membrane 201b mounted at one end thereof. The nosepiece 201a surrounds a coupling fluid cavity 201c. The assembly comprising the nosepiece 201a and lock plate 205a is mounted onto the scan head 206 via the bayonet style lock system.

The coupling fluid cavity 201c surrounds a transducer 202a, which is attached to the support arm 203. The transducer 202a is connected to a transducer coaxial cable 202b, which is connected at the opposite end to the circuit board 224. The nosepiece 201a includes a fill port to fill the coupling fluid cavity 201c with a coupling fluid. The fill port is sealed by a fill port screw 204. A molded rubber seal 207 is mounted on the support arm 203 and disposed between the fluid cavity 201c and a pivot frame 208.

A bearing assembly including a bearing preload screw 209, precision radial ball bearings 208a, and a fixing screw 210a affixes the armature assembly 240, to the pivot frame 208, with low radial drag and virtually no radial or axial play. A yoke 212 is provided straddling the support arm 203 and fixed to the rotor 218 with rotor adhesive pins 214.

Figure 12:
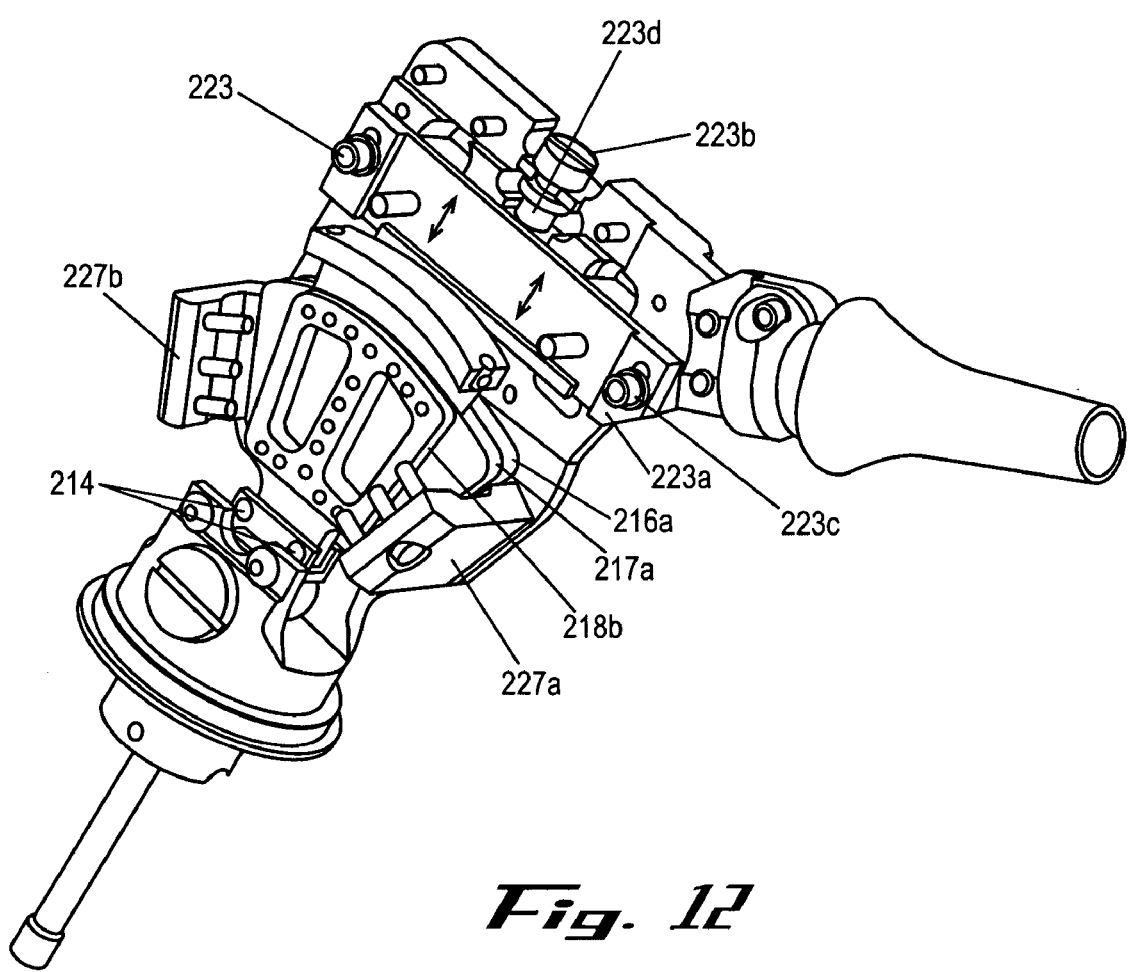
FIG. 12 is a perspective view of a portion of the scanhead of FIG. 9.

A partial assembly 250 of the scan head 206 shown in FIG. 12 includes a rear backing iron 216a, a pair of backing iron posts 227a and 227b, rear field magnet 217a. A magnet wire coil 218b wound around the rotor 218 to form the armature of the torque motor. An optical encoder code track 219 is attached to one end of the rotor 218 such that it is at all points tangent to the motion of the torque motor. An optical encoder read head 220 is affixed to an encoder adjustment slide 223a as shown in FIG. 12. The encoder adjustment slide 223a is fitted to the chassis 215 so that it can slide allowing adjustment of the optical read head 220 with respect to the encoder code track 219, which is fixed to the armature 240. The movement is precise and controlled, and when the encoder read head 220 is in the optimal position such that maximum signal strength is obtained at the encoder read head 220, the read head adjustment slide 223a is locked in place with read head locking screws 223c. Because the optical encoder is focused, it can be positioned at a known distance from the reflective encoder code track 219. This distance corresponds to a maximum encoder signal. A helical spring 223d coupled to the read head adjustment screw 223b helps prevent backlash. The optical read head 220 combined with the encoder code track 219 allows the position of the armature 240 to be recorded with an accuracy of 1 μm. A pair of optical limit switches 221a are provided on the circuit board 224 for determining the absolute position of the armature 240 with respect to the chassis 215, and to protect against over travel of the armature 240. A reflective surface 221b attached to the rotor 218 reflects signals from the optical limit switch 221a.

As shown in FIGS. 9 and 10, the chassis 215 includes a quick release hard mount jack 222a. This mechanism is part of a quick release assembly, which is described in greater detail below with reference to FIGS. 13 and 14.

A case comprising a case top 233, a case bottom 234 and a case gasket 228 provides a fluid-tight seal around the internal components of the scan head 206. The case top 233 and case bottom 234 as well as the case gasket 228 are coated with an electrically conductive coating 251 to improve RF shielding.

Figure 11:
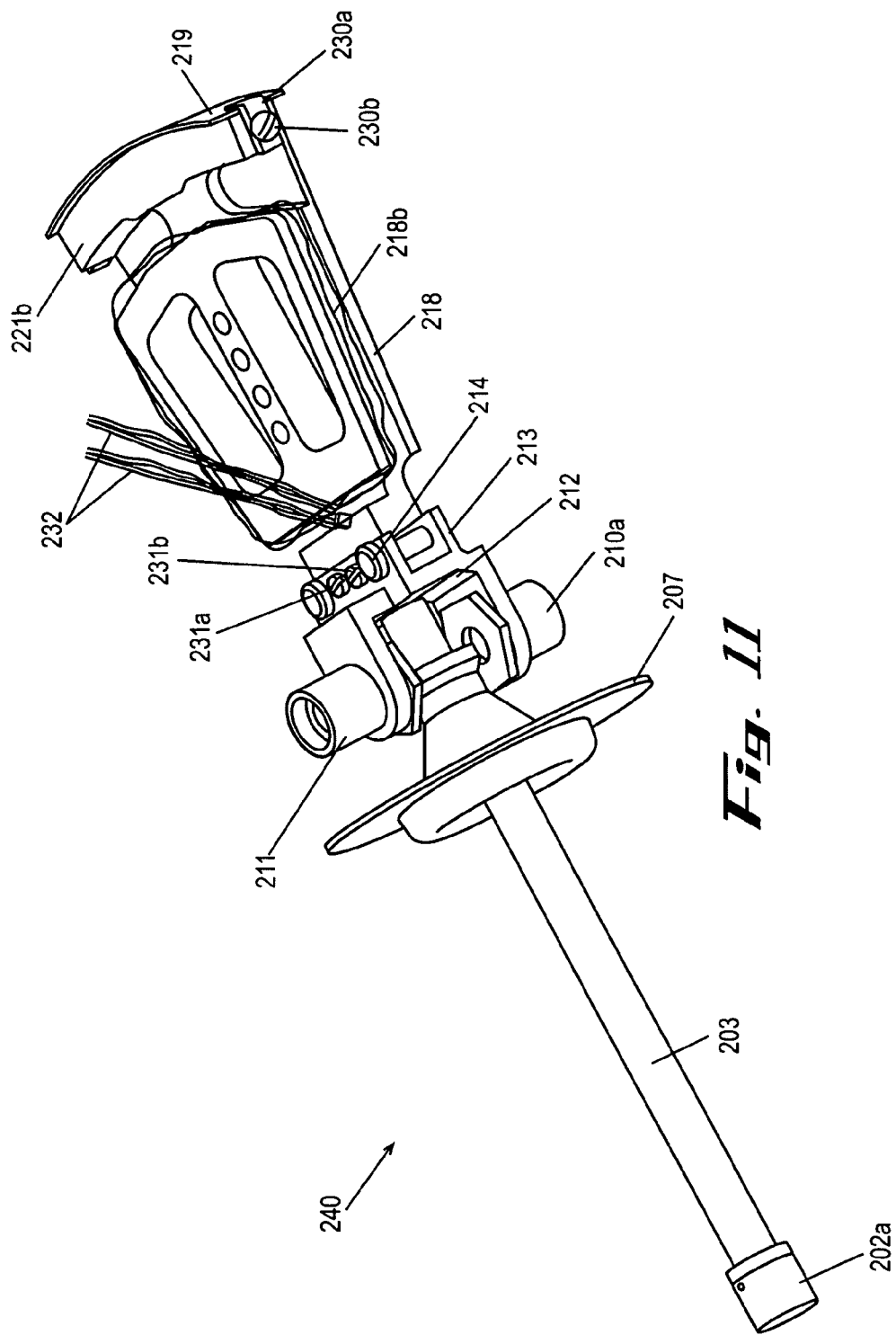
FIG. 11 is a perspective view of an armature assembly in the scanhead of FIG. 9.

Referring to FIG. 11, the armature 240, the support arm 203, the transducer, 202a, and the molded seal 207, are shown in more detail. The armature 240 can be fabricated from precision machined components, which facilitates manufacturability, reduces cost, and improves performance compared to the composite construction used in the embodiment referred to above. The support arm 203 is removable and can be mounted via the support arm mount 213 and two shoulder bolts 231a and 231b, which locate into precision holes in the yoke 212 and the rotor 218. It will be recognized therefore that a damaged transducer 202a and/or molded seal 207 may be replaced without replacing the entire armature 240.

The encoder code track 219 is made from a spring steel substrate. The encoder code track 219 can be installed using a technique which avoids prebending of the encoder code track 219. Prebending may damage the encoder code track 219. Two encoder code track retainers 230a hold the encoder code track 219 at each end, forcing the spring steel to take the exact curvature of the rotor 218. The encoder track retainers 230a are fixed in place using screws 230b. Alternatively, a light string may be tied around screws 230b and adhered, using, for example, a glue, to the ends of the encoder code track 219

The scanhead 206 of this embodiment provides a sweep angle greater than 22 degrees included. The sweep angle refers to the motion of the transducer 202a defined by the Hall sensor 13, the two Hall sensor magnets 26 and 26a, and the limit switches 221a. In addition to the increased sweep angle due to the removable support arm 203, the length of the support arm 203 may be changed, during manufacture or after, such as during field service, to accommodate different imaging requirements. The support arm 203 can be a length such that the transducer 202a is approximately 20 percent farther from the pivot point 154 than the encoder code track 219 (see FIG. 9). This configuration provides a scan width of over 15 mm measured at the transducer 202a.

The scan head 206 in this embodiment is assembled on the rigid chassis 215. The scan head 206 can be assembled to complete functionality on the chassis 215 so that testing can be performed without the case 233, 234 in place. The design of the chassis 215 therefore allows verification of wire routing and strain relief, electrical inspection, tuning of the optical encoder read head 220, and function verification of the limit switches 221a.

Figure 13:
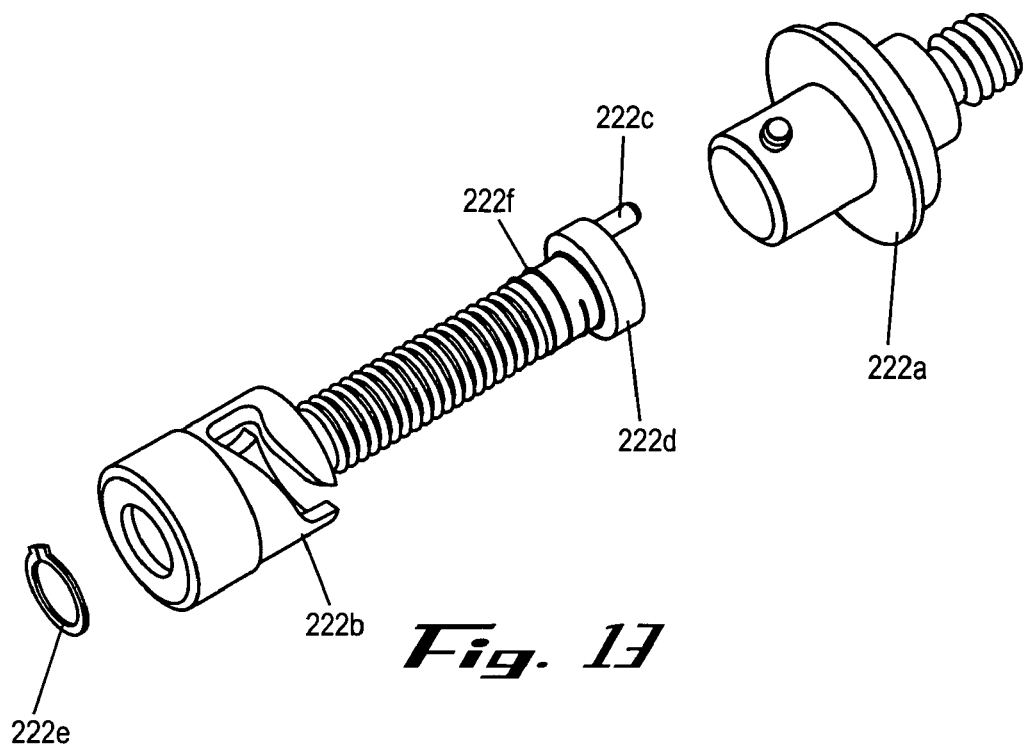
FIG. 13 is an exploded view of a release assembly of the scanhead of FIG. 9.
Figure 14:
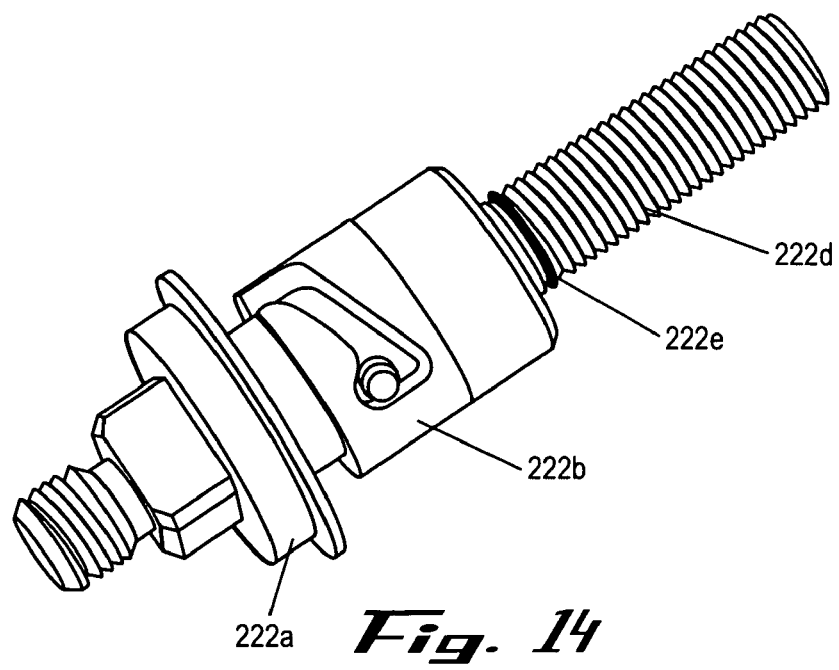
FIG. 14 is an assembled view of the quick release assembly of FIG. 13.

Referring to FIGS. 13 and 14, the quick release hard mount is shown in more detail. The quick release mechanism uses a spring loaded bayonet lock to quickly mount and remove the scanhead 206. The quick release hard mount plug 222b includes a locating pin 222c at the end proximal to the quick release hard mount jack 222a. The hard mount plug 222b includes a quick release upper feature 222d adjacent to the locating pin 222c, and a helical spring 222f adjacent to the locating pin 222c. The locating pin 222c allows the scanhead 106 to be mounted and remounted in precise 90 degree increments. A retaining ring 222e bears against the hard mount plug 222b when attached to the hard mount jack 222a as seen in FIG. 14.

Figure 15:
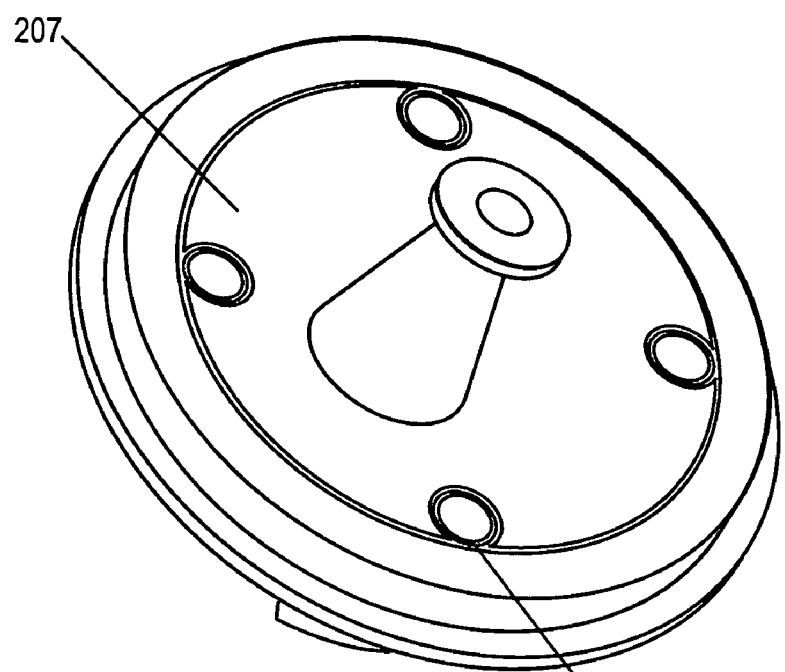
FIG. 15 is a perspective view of a seal of the scanhead of FIG. 9.
Figure 16:
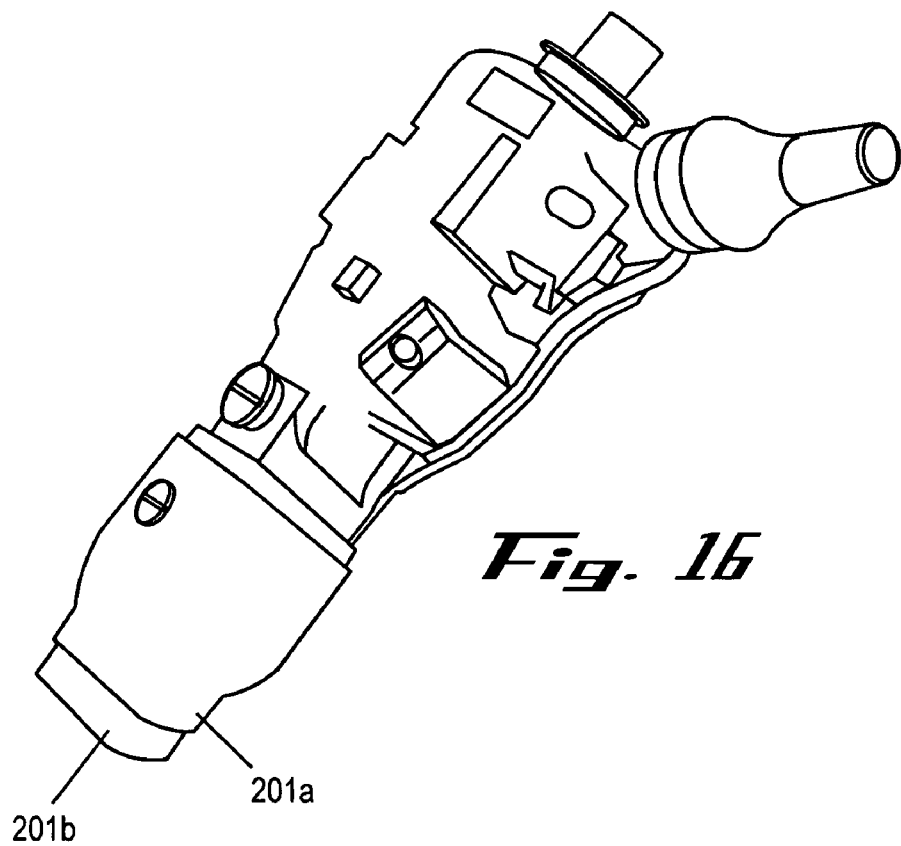
FIG. 16 is a perspective view of the scanhead of FIG. 9 in a testing configuration.

Referring to FIG. 15, the nose 205 is shown in more detail. The nose 205 includes gasket bosses 206b, which prevent damage to the molded seal 207 (FIG. 11) when clamping the molded seal 207 between the nose 205 and the pivot frame 208. The seal 207 can be made from a soft, flexible elastomer. The molded shape provides a centered rest position and eliminates stretch mode deformation of the seal 207 during operation. By contrast, a flat seal undergoes both bending and stretching during operation, resulting in two distinct loads on the motor, which can be difficult to compensate for. The molded seal 207 can be designed like a shifter boot on an automobile's gear shift. It undergoes only bending deformation, which results in a lower and more uniform load on the motor.

The scanhead 206 includes an integral circuit board 224 that integrates motor control functions, position monitoring functions, and the transmission and reception of RF signals. In addition, the circuit board 224 houses the optical limit switches 221a. The circuit board 224 can be prefabricated and tested. The circuit board 224 allows the routing of the transducer coaxial cable 202b and the motor wires 232 to be made with a minimal drag on the motor by placing the connection points nearly over the pivot point.

The case 233, 234 can be non-load bearing and can be a purely protective part of the scanhead 206. It serves to waterproof and keep the internal components of the scanhead 206 free of contamination. The case 233, 234 can be secured to the chassis 215 by screws. Alternatively, the two halves 233, 234 of the case may be glued, or otherwise adhered, together to make the scanhead 206 tamper and water resistant.

The nosepiece 201a may include a disposable acoustic window. Referring to FIGS. 17A, 17B, 18, 19A, 19B and 20-23, the structure of the nosepiece 320 and acoustic window 330 are shown. The acoustic window 330 is similar to the acoustic window 125 described above. The nosepiece 320 includes a fill port 322 for receiving fluid. The nosepiece 320 has a shoulder 324 at the end proximal to the acoustic window 330 when attached. A recess 326 and a lip 328 are located adjacent the shoulder 324 for forming a snap fit with the acoustic window 330.

Figure 17A:
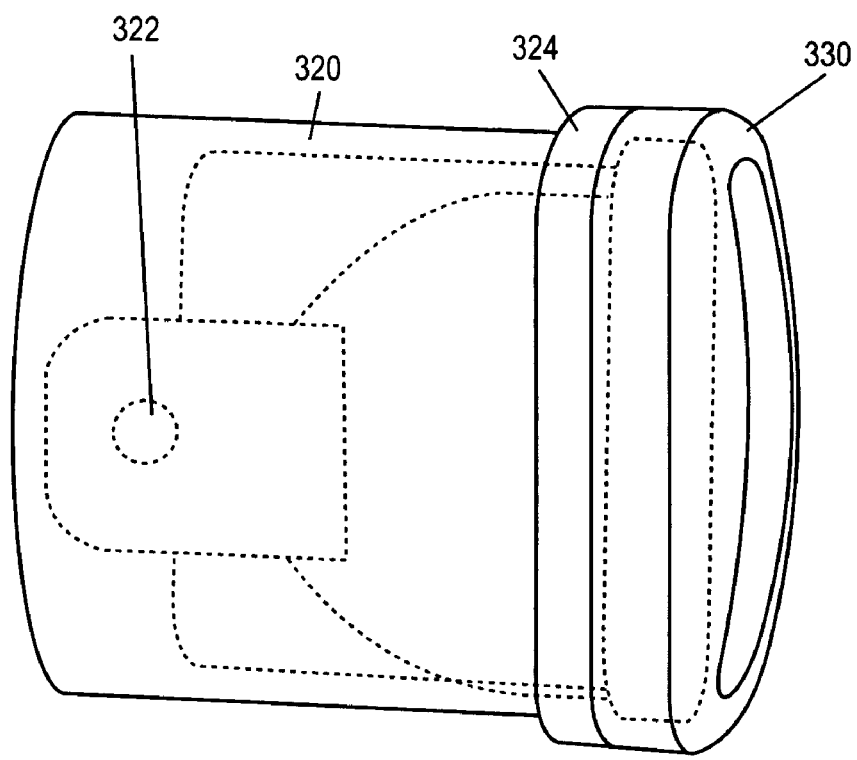
FIG. 17A is a perspective view of a nosepiece for the scanhead of FIG. 9.
Figure 17B:
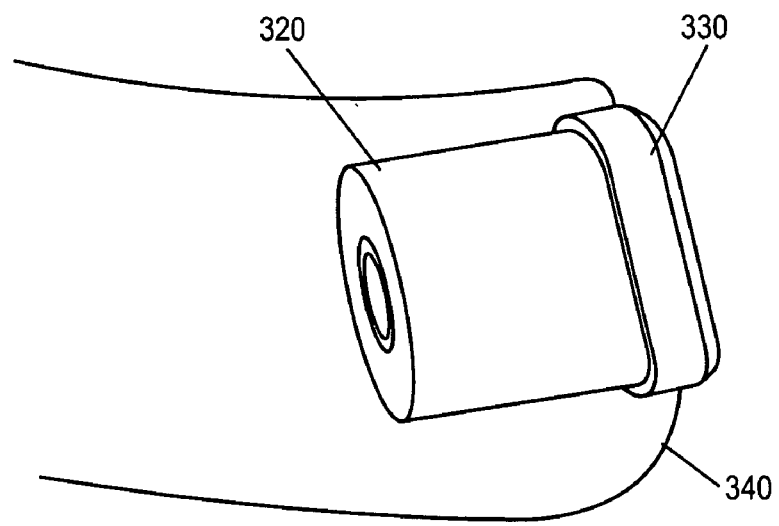
FIG. 17B is a perspective view of the nosepiece of FIG. 17 shown with an optional shroud.
Figure 18:
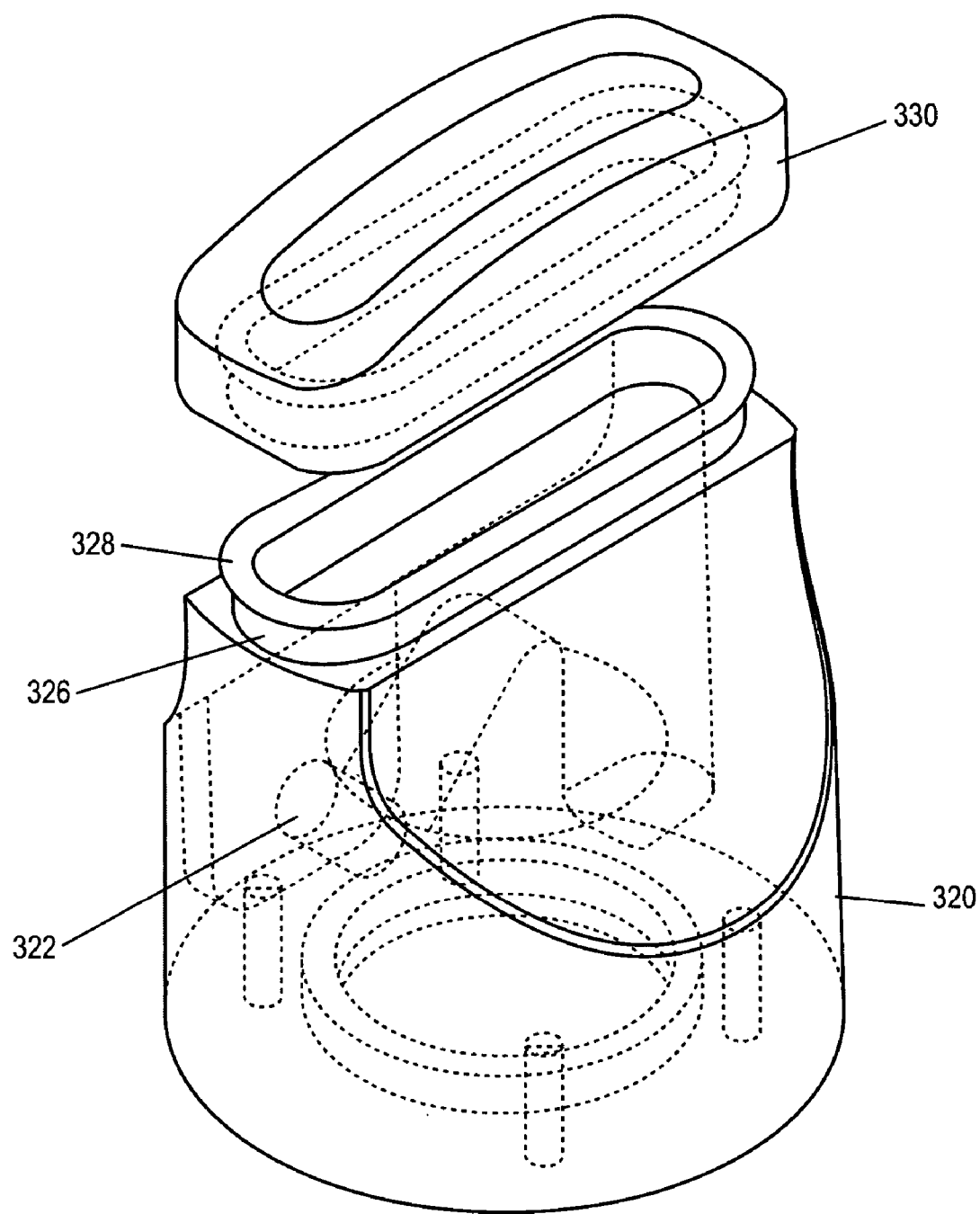
FIG. 18 is another view of the nosepiece of FIG. 17 in a separated position.
Figure 19A:
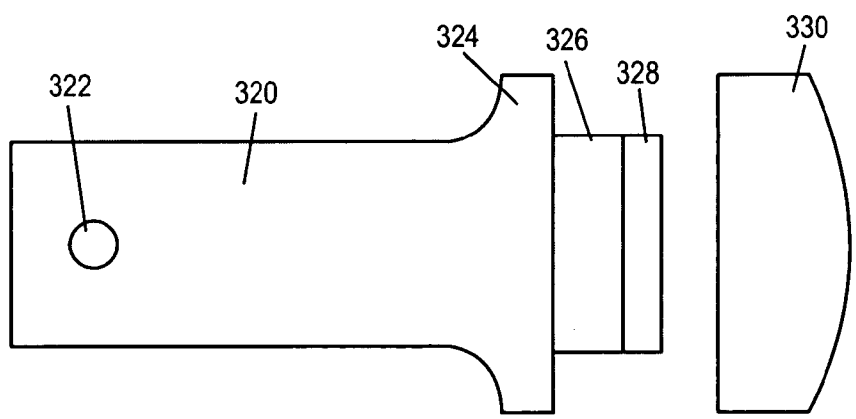
FIG. 19A is side view of FIG. 17.
Figure 19B:
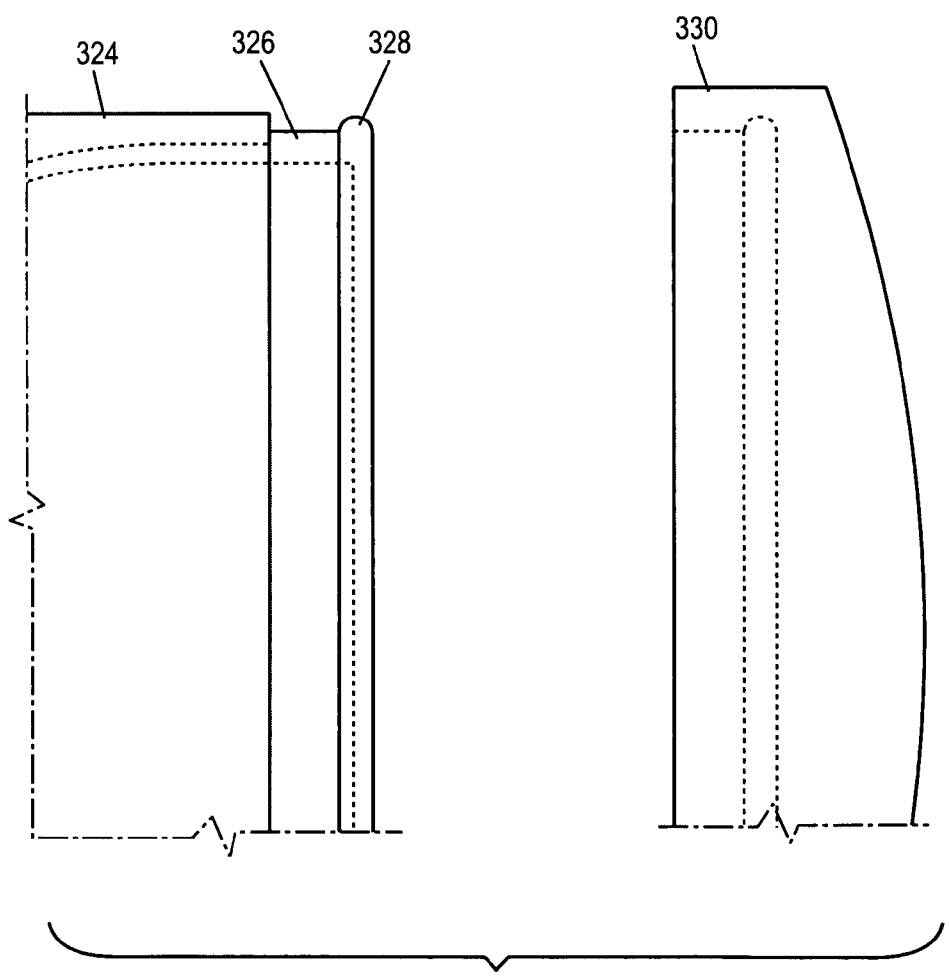
FIG. 19B is a detail view of FIG. 19A.

FIG. 17B shows the nosepiece 320 with an optional shroud 340 attached. The shroud 340 attaches to the acoustic window 330 to protect the nosepiece 320 and scanhead 206 from contamination by liquid or biological material.

Figure 21:
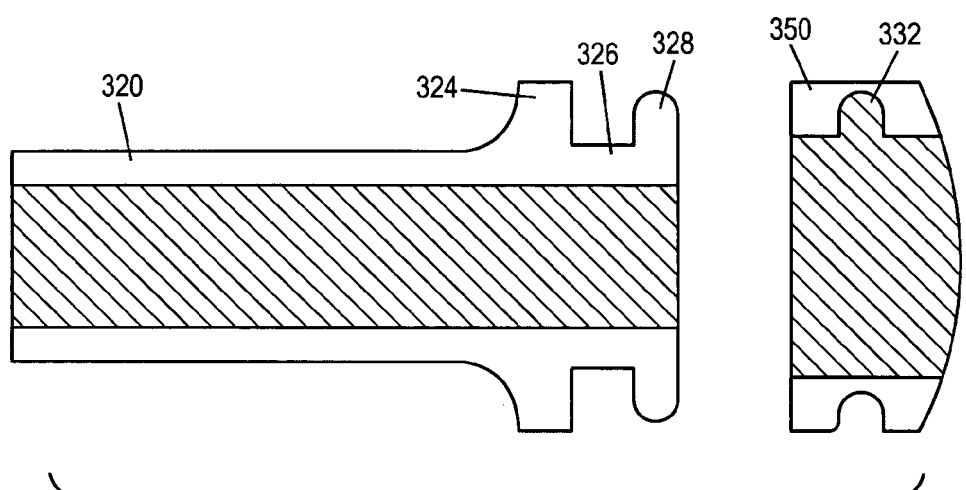
FIG. 21 is a cutaway of FIG. 17.
Figure 22:
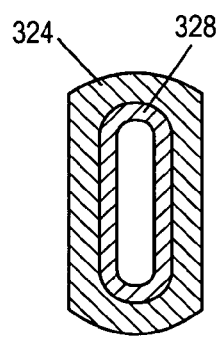
FIG. 22 is an end view of nosepiece of FIG. 17.
Figure 23:
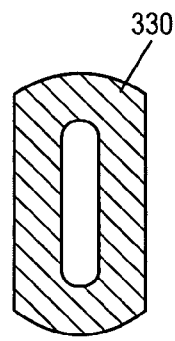
FIG. 23 is an end view of acoustic window of FIG. 17.

As shown in FIG. 21, the acoustic window 330 includes a groove 332 with a shape complementary to the lip 328 in the nosepiece 320.

The acoustic window 330 can be designed to overcome the specific challenges of encapsulating a high frequency high-resolution ultrasonic probe in a variety of demanding environments. The acoustic window 330 provides an inexpensive means for protecting the transducer and allowing imaging in a sterile environment without unduly compromising acoustic performance. The acoustic window 330 can be constructed from a molded plastic frame comprising a fluid tight mechanical snap-on attachment structure. The acoustic window 330 can be a molded, disposable element, which 'snaps' onto a permanent machined nosepiece, yielding the fluid filled encapsulated nose of the probe. Tools are not required to remove or attach the acoustic window to the nosepiece. For example, the shape of the acoustic window permits attachment to the nosepiece of the transducer using a simple rolling motion. The acoustic window can be any shape depending upon the nosepiece to be covered. A thin film of a sonolucent material forms a membrane 352 that can be attached to the front face of a frame 350. The frame 350 and the membrane 352 comprise the acoustic window 330.

The characteristics and thickness of the material forming the membrane of the acoustic window are chosen to suit the characteristics of the specific probe to be encapsulated. Sonolucent materials, for example those disclosed in U.S. Pat. Nos. 5,479,927; 5,983,123; and 6,574,499, which are incorporated by reference in their entireties, can be used to produce the membrane 352 of the acoustic window 330. In one aspect, the sonolucent material can be a polyester, a polycarbonate, an acrylic, a thermoplastic elastomer, or a silicone elastomer. Examples of sonolucent materials include, but are not limited to, Surlyn® ionomers, such as Surlyn® 8940, and Kapton®, available from E. I. Du Pont de Nemours and Company, Wilmington, Del.; polymethyl pentenes, such as TPX® MX-002, TPX® 95 and MX-004, available from Mitsui & Co., Tokyo, Japan; Teflon®, Mylar®, polyethylene, such as low density polyethylene, polycarbonate, polypropylene, and various polyurethane films. In one embodiment, the sonolucent material can be extruded to a certain thickness and heat welded to the frame 350 of the acoustic window 330 to form a fluid tight seal. The thickness of the membrane 352 will vary depending upon the sonolucent material selected. In one aspect, the membrane 352 has a thickness of less than or equal to 25 µm. In another embodiment, the thickness of the membrane 352 can range from 1 µm to 25 µm. The technology used for sealing the membrane 352 to the frame 350 will vary depending on the sonolucent material selected. Examples of methods for sealing the membrane 352 to the frame 350 include, but are not limited to, adhesives, welding techniques (e.g., RF, ultrasonic, and thermal), and mechanical seals.

Figure 20:
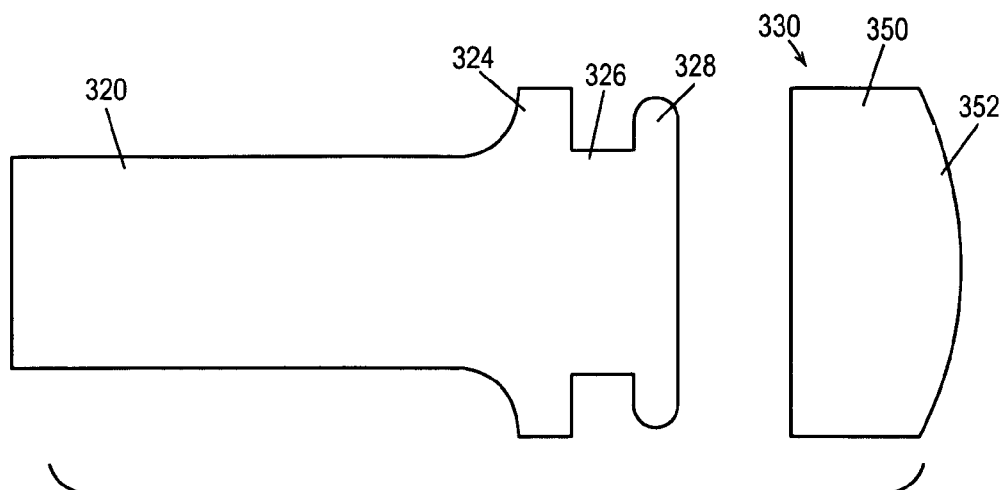
FIG. 20 is a cross section of FIG. 17.

Referring to FIGS. 20 and 21, the snap structure comprises a groove 332 in the frame 350. The nosepiece 320 to which the acoustic window 330 will attach incorporates a lip 328. The lip 328 can be slightly oversized negative with respect to the groove 332 in the frame 330. The acoustic window 330 can be pressed onto the nosepiece 320 so that a positive fit is obtained when fully in place due to the seal formed between the lip 328 and the groove 332. This fit is also fluid tight due to the interference type fit of the groove 332 and lip 328. Before fitting the acoustic window 330 onto the nosepiece 320, the nosepiece can be partially filled with a coupling fluid. Examples of coupling fluid include, but are not limited to, water, ethylene glycol, triethylene glycol, light paraffin oil and various aqueous solutions of glycols. After fitting the acoustic window 330, air bubbles can be removed and the nosepiece/acoustic window assembly fully filled with coupling fluid via the fill port 322 located on the side of the nosepiece 320.

For environments requiring complete isolation of the probe from the surroundings, a sheathed version of the acoustic window 330 includes a heat sealed sheath 340 of polyethylene film that can be designed to fit back over the probe and up the cable. The sheath can be formed as part of the disposable acoustic window 330, so that when sterilization is desired the entire window and sheath can be removed and discarded.

Figure 24:
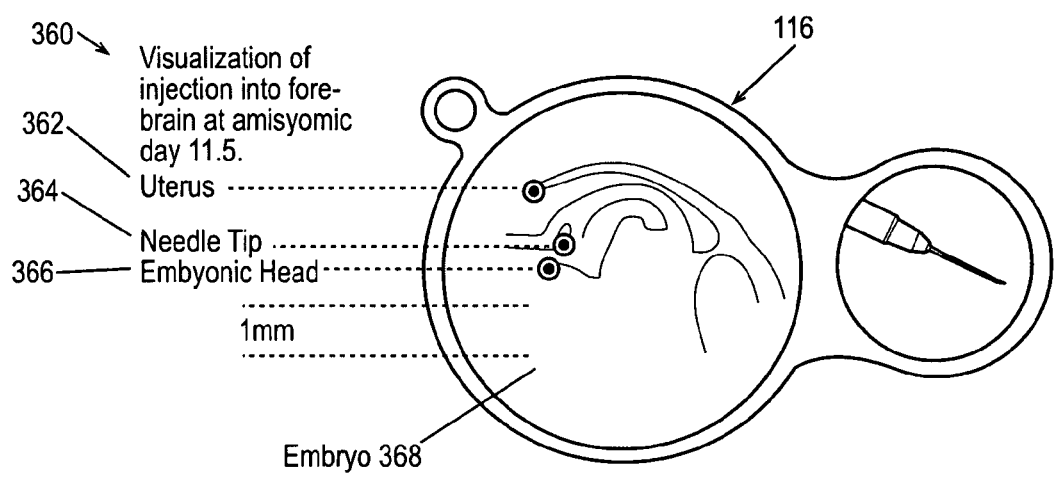
FIG. 24 is a screen shot depicting an image on the display.

In an alternative embodiment, the high-frequency, high frame-rate ultrasound imaging system may be used to image a syringe, catheter, or other invasive element inserted into a subject. FIG. 24 is a screen shot depicting an image 360 on the display 116. The image includes an embryo 368. The embryo 368 includes a head 366 and a uterus 362. The ultrasound system 131 can be used to visualize and guide the needle 364 as it enters the uterus 362 of the embryo 368.

Figure 25:
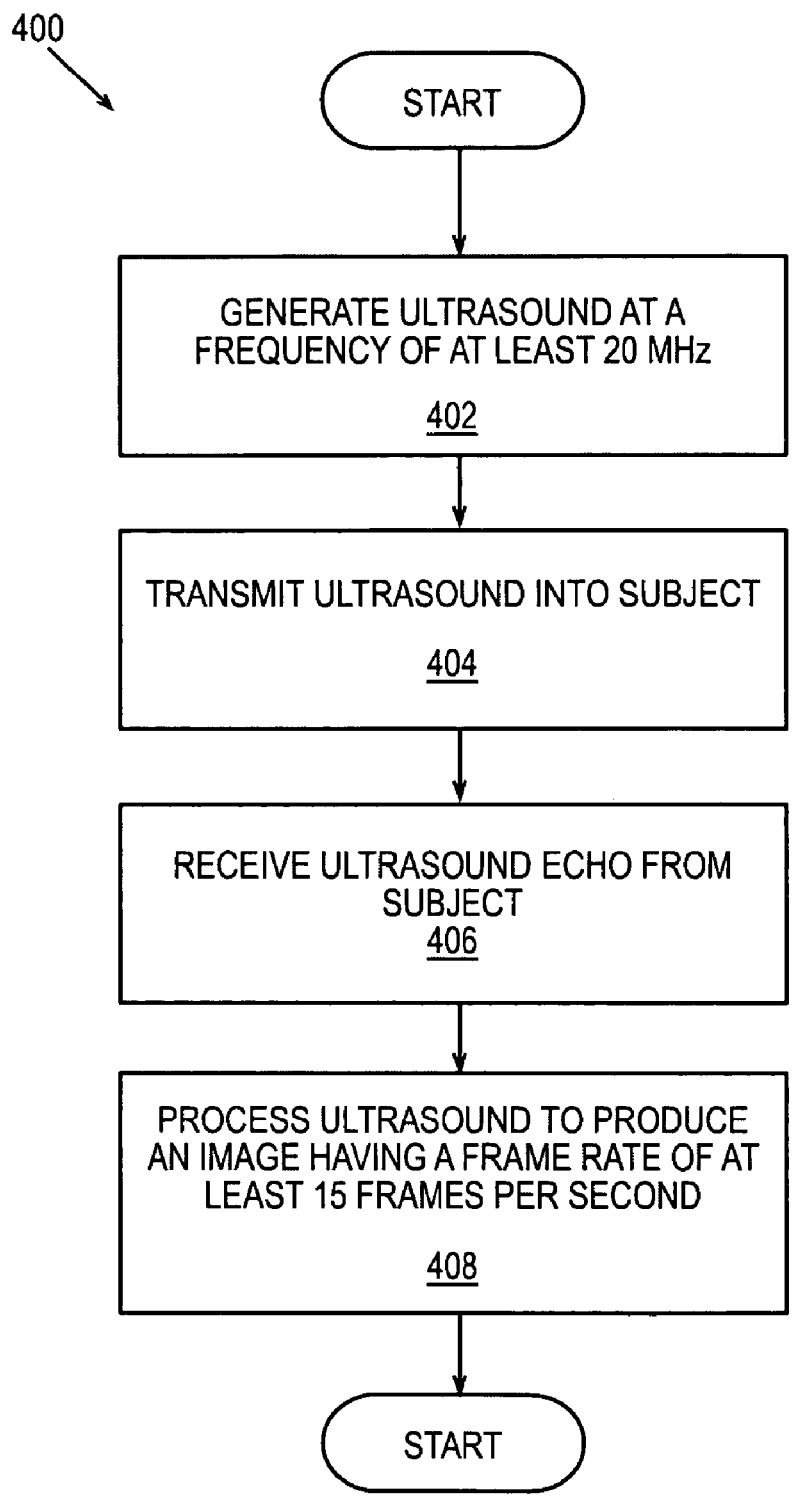
FIG. 25 is a flow chart illustrating the operation of one aspect of the high-frequency, high frame-rate ultrasound imaging system.

FIG. 25 is a flow chart illustrating the operation of one aspect of the high-frequency, high frame-rate ultrasound imaging system. The blocks in the flow chart may be executed in the order shown, out of the order shown, or concurrently. In block 402, the transducer 8 generates ultrasound energy at a frequency of at least 20 MHz.

Figure 1:
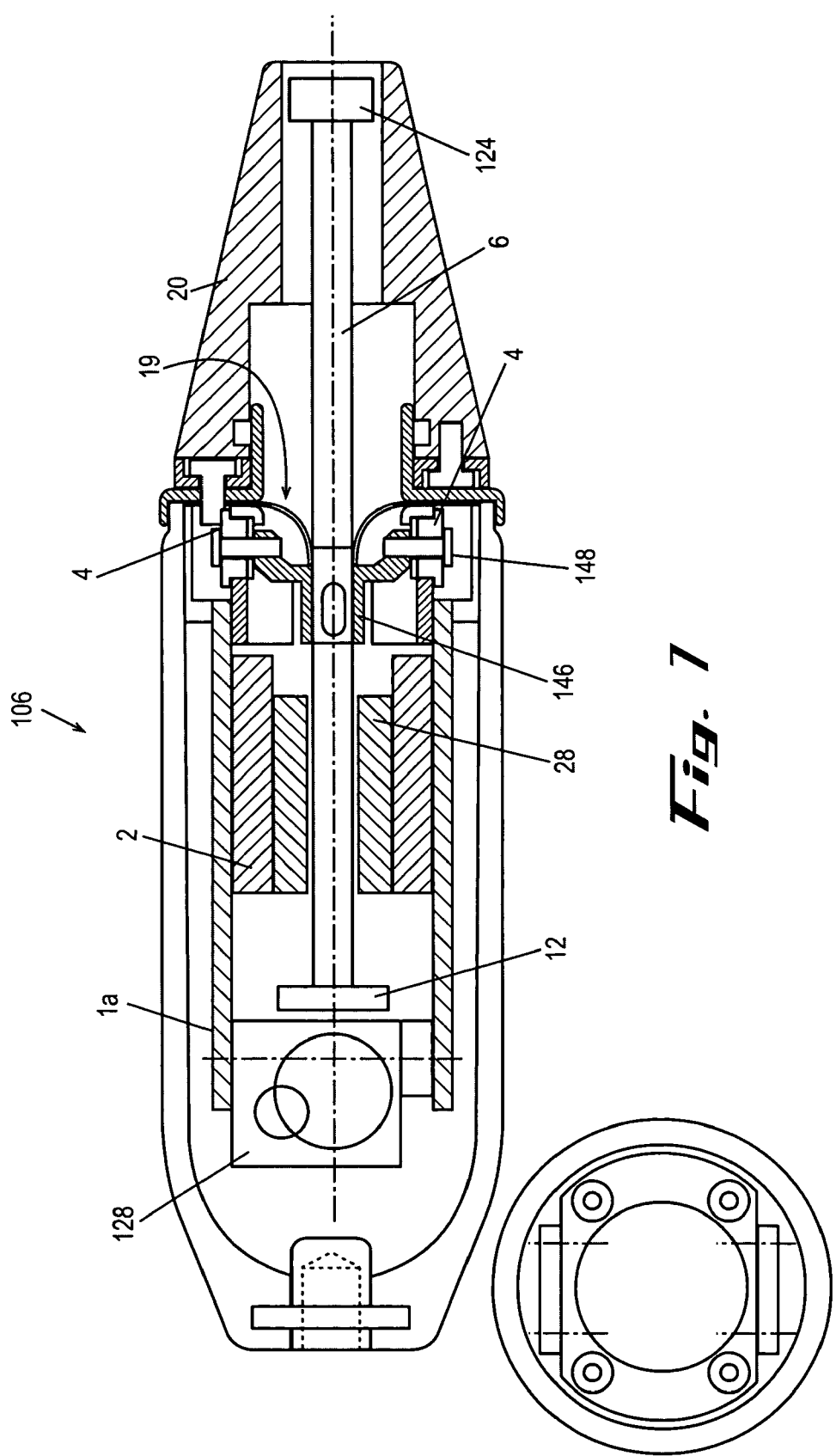

In block 404, the ultrasound energy is transmitted by the transmit subsystem 118 into the subject 114 (FIG. 1). In block 406, the receive subsystem 120 receives the returned ultrasound echo pulses 104 and communicates the received ultrasound to the control subsystem 127 for processing by the processor 134 and the scan converter 129.

In block 408, the received ultrasound is processed by the processor 134 and the scan converter 129, under the direction of the software 123, to generate an image on the display 116. The image has a frame rate of at least 15 frames per second (fps).

Although the high-frequency, high frame-rate ultrasound imaging system has been described with reference to certain specific embodiments, various modifications thereof will be apparent to those skilled in the art without departing from the scope of the high-frequency, high frame-rate ultrasound imaging system as outlined in the claims appended hereto.

What is claimed is:

1. A scanhead for use with an ultrasound imaging system, comprising:
 a transducer assembly comprising a single element ultrasonic transducer that is configured to generate ultrasound at a frequency of at least 20 megahertz (20 MHz), to transmit at least a portion of the generated ultrasound into a subject and to receive ultrasound energy from the subject;
 an elongate member having a proximal end, wherein the elongate member is configured to pivot about a pivot axis spaced from the proximal end, and wherein the transducer assembly is non-rotatably coupled to the proximal end of the elongate member;
 a means for oscillating the transducer along a reciprocating convex arcuate path at a frequency of at least 7.5 Hz, wherein a portion of the means for oscillating is fixed relative to the elongate member and moves along a reciprocating arcuate route remote from the reciprocating arcuate path of the transducer such that movement of the portion of the means for oscillating causes a complementary and opposite movement of the transducer, and wherein the reciprocating arcuate path of the transducer is co-planer to the reciprocating arcuate route of the portion of the means for oscillating; and
 a means for sensing the spatial position of a proximal end of the portion of the means for oscillating along the reciprocating Arcuate route to determine the position of he transducer along its arcuate path.

2. The scanhead of claim 1, wherein the transducer is a broadband transducer.

3. The scanhead of claim 1, wherein the transducer assembly and at least a portion of the elongate member are located within an enclosed volume, and wherein the enclosed volume is at least partially filled with a fluid.

4. The scanhead of claim 3, wherein the fluid has an impedance substantially similar to the impedance of tissue.

5. The scanhead of claim 3, wherein the fluid is a glycol.

6. The scanhead of claim 3, wherein the fluid is water.

7. The scanhead of claim 3, wherein the fluid is selected from the group consisting of: water, ethylene glycol, triethylene glycol, and light paraffin oil.

8. The scanhead of claim 3, wherein the enclosed volume is partially defined by an acoustically penetrable membrane and wherein the acoustically penetrable membrane is positioned such that at least a portion of the generated ultrasound can pass therethrough the membrane before being transmitted into the subject.

9. the scanhead of claim 8, further comprising a sealing membrane that defines at least a portion of the enclosed volume.

10. the scanhead of claim 9, wherein the sealing membrane is sealed relative to the elongate member at the pivot axis.

11. the scanhead of claim 10, wherein the sealing membrane is configured to have a reduced stretch deformation when the elongate member is oscillated within the enclosed volume.

12. The scanhead of claim 9, wherein the sealing membrane comprises a flexible elastomer.

13. The scanhead of claim 9, wherein the sealable membrane comprises a flexible elastomer.

14. The scanhead of claim 8, wherein the acoustically penetrable membrane has a thickness of about 0.9 microns (μm) to about 60.0 microns (μm).

15. The scanhead of claim 8, wherein the acoustically penetrable membrane is sealably attached to a frame member, and wherein the frame member and the membrane comprise the same material.

16. The scanhead of claim 8, wherein the acoustically penetrable membrane has an acoustic impedance that is substantially the same as the acoustic impedance of the fluid.

17. The scanhead of claim 8, wherein the acoustically penetrable membrane has an impedance of between about 1.0 megaRayles and 3.3 megaRayles.

18. The scanhead of claim 17, wherein the acoustically penetrable membrane has an impedance of between about 1.5 megaRayles and 1.8 megaRayles.

19. The scanhead of claim 8, wherein the acoustically penetrable membrane comprises a material selected from the group consisting of: polyester, polycarbonate, acrylic, thermoplastic elastomer, silicone elastomer, laytex elastomer, Surlyn® ionomer, Surlyn® 8940, Kapton®, polymethyl pentene, TPX® MX-002, TPX® 95, MX-004; Teflon®, Mylar®, polyethylene, polytetrafluoroethylene, polycarbonate, polypropylene, and polyurethane films.

20. The scanhead of claim 19, wherein the polyethylene is low density polyethylene (LDPE).

21. The scanhead of claim 8, wherein at least a portion of the transducer can contact at least a portion of the interior surface of the membrane during its movement along the reciprocating arcuate path.

22. The scanhead of claim 1, wherein the transducer can be moved along the reciprocating arcuate path over a distance of about 15 millimeters (mm) or less.

23. The scanhead of claim 1, wherein the transducer can be moved along the reciprocating arcuate path over a distance of about 10 millimeters (mm) or less.

24. The scanhead of claim 1, wherein the transducer can be moved along the reciprocating arcuate path over an angle of about 22 degrees or less.

25. The scanhead of claim 1, wherein the transducer can be moved along the reciprocating arcuate path at a frequency of at least 15 Hz.

26. The scanhead of claim 1, wherein the transducer can be oscillated along the reciprocating arcuate path at a frequency of at least 30 Hz.

27. The scanhead of claim 1, further comprising a position encoder configured to determine the position of the transducer along its reciprocating arcuate path.

28. The scanhead of claim 27, wherein the position encoder is configured such that the position of the transducer can be accurately tracked along the reciprocating arcuate path to within about 1.0 micron (μm) of the actual transducer position.

29. The scanhead of claim 1, wherein the means for oscillating comprises a limited angle motor.

30. The scanhead of claim 29, wherein the limited angle motor is a moving coil type torque motor.

31. The scanhead of claim 29, wherein the limited angle motor can oscillate the transducer along the reciprocating arcuate path at a speed of at least about 10 Hz.

32. The scanhead of claim 31, wherein the limited angle motor can oscillate the transducer along the reciprocating arcuate path at a speed of at least about 15 Hz.

33. The system of claim 32, wherein the limited angle motor can oscillate the transducer along the reciprocating arcuate path at a speed of at least about 30 Hz.

34. The scanhead of claim 1, wherein the transducer is configured to generate ultrasound at a frequency of between about 25 MHz and about 60 MHz.

35. The scanhead of claim 1, wherein the transducer is configured to generate ultrasound at a frequency of at least about 25 MHz.

36. An ultrasound imaging system, comprising:
the scanhead of claim 1; and
a processor configured to process the received ultrasound to provide an image having a frame rate of at least 15 frames per second (fps).

37. The system of claim 36, wherein the processor is further configured to produce an ultrasound image having a spatial resolution of less than about 100 microns (μm).

38. The system of claim 37, wherein the processor is further configured to produce an ultrasound image having a spatial resolution of about and between 75-100 microns (μm).

39. The system of claim 37, wherein the processor is further configured to produce an ultrasound image having a spatial resolution of about and between 30-100 microns (μm).

40. The system of claim 36, wherein the transducer can be oscillated along the reciprocating arcuate path at a frequency of at least 15 Hz, and wherein the processor is configured to provide an image having a frame rate of at least 30 fps and a spatial resolution of less than about 100 microns (μm).

41. The system of claim 36, wherein the transducer can be oscillated along the reciprocating arcuate path at a frequency of at least 30 Hz and wherein the processor is configured to provide an image having a frame rate of at least 60 fps and a spatial resolution of less than about 100 microns (μm).

42. The ultrasound imaging system of claim 1, wherein the scanhead is configured for extra-vascular imaging applications.

43. An ultrasound imaging system, comprising:
the scanhead of claim 1;
a processor configured to process the received ultrasound to provide an image having a frame rate of at least 15 frames per second (fps); and
a means for positioning the transducer to within about 1 micron (μm) of a predetermined location along the reciprocating arcuate path.

44. The ultrasound imaging system of claim 43, wherein the processor is further configured to provide a pulsed-wave Doppler image.

45. The ultrasound imaging system of claim 43, wherein the processor is further configured to provide an M-Mode image.

46. A method for producing an ultrasound image, comprising:
a) providing a scanhead, comprising:
i) a transducer assembly comprising a single element ultrasonic transducer;

ii) an elongate member having a proximal end, wherein the elongate member is configured to pivot about a pivot axis spaced from the proximal end, and wherein the transducer assembly is non-rotatably coupled to the proximal end of the elongate member;

iii) a means for oscillating the transducer along a reciprocating convex arcuate path, wherein a portion of the means for oscillating is fixed relative to the elongate member and moves along a reciprocating arcuate route remote from the reciprocating arcuate path of the transducer such that movement of the portion of the means for oscillating causes a complementary and opposite movement of the transducer, and wherein the reciprocating arcuate path of the transducer is co-planer to the reciprocating arcuate route of the portion of the means for oscillating; and iv) a means for sensing the spatial position of a proximal end of the portion of the means for oscillating along the reciprocating Arcuate route to determine the position of the transducer along its arcuate path.

b) generating ultrasound at a frequency of at least about 20 megahertz (20 MHz) using the transducer;

c) transmitting at least a portion of the generated ultrasound into a subject from a location external to the subject;

d) receiving ultrasound energy from the subject;

e) oscillating the transducer along the reciprocating arcuate path at a frequency of at least 7.5 Hz during the generation, transmission and receipt of the ultrasound; and f) processing the received ultrasound to provide an image having a frame rate of at least 15 frames per second (fps).

47. The method of claim 46, wherein the subject is a small animal.

48. The method of claim 47, wherein the small animal is a mouse or a rat.

49. The method of claim 46, wherein the subject is an embryo.

50. The method of claim 46, further comprising using ultrasound in a frequency range of 20 MHz to 60 MHz.

51. The method of claim 46, wherein the transducer is moved along the reciprocating arcuate path at a frequency of at least 30 Hz, and wherein the provided image has a frame rate of at least 60 fps.

52. The method of claim 46, wherein the position of the transducer is accurately tracked along the reciprocating arcuate path to within about 1.0 micron ($\mu$m) of the actual transducer position using a position encoder.

53. The method of claim 46, further comprising positioning the transducer to within about 1 micron ($\mu$m) of a predetermined location along the reciprocating arcuate path.

54. The method of claim 53, wherein the provided image is a pulsed-wave Doppler image.

55. The method of claim 53, wherein the provided image an M-Mode image.

* * * * *